(12) United States Patent
Zhu et al.

(10) Patent No.: US 10,072,035 B2
(45) Date of Patent: Sep. 11, 2018

(54) PHENANTHROLINE PHOSPHONIC ACID DERIVATIVE AND PREPARATION METHOD THEREFOR AND APPLICATION THEREOF

(71) Applicant: Guangzhou Beryl Therapeutics, Inc, Guangdong (CN)

(72) Inventors: Yue Zhu, Changchun (CN); Yuzhen Liao, Changchun (CN); Li Zhang, Changchun (CN); Xu Bai, Changchun (CN)

(73) Assignee: GUANGZHOU BERYL THERAPEUTICS, INC, Guangdong (CN)

( * ) Notice: Subject to any disclaimer, the term of this patent is extended or adjusted under 35 U.S.C. 154(b) by 0 days.

(21) Appl. No.: 15/302,568

(22) PCT Filed: Apr. 10, 2015

(86) PCT No.: PCT/CN2015/076273
§ 371 (c)(1),
(2) Date: Oct. 7, 2016

(87) PCT Pub. No.: WO2015/154716
PCT Pub. Date: Oct. 15, 2015

(65) Prior Publication Data
US 2017/0029452 A1 Feb. 2, 2017

(30) Foreign Application Priority Data

Apr. 10, 2014 (CN) .......................... 2014 1 0142608

(51) Int. Cl.
| | | |
|---|---|---|
| C07F 9/60 | (2006.01) | |
| C07F 9/6561 | (2006.01) | |
| C07F 9/6574 | (2006.01) | |
| C07F 9/6558 | (2006.01) | |
| C07F 9/6571 | (2006.01) | |

(52) U.S. Cl.
CPC ............ *C07F 9/65742* (2013.01); *C07F 9/60* (2013.01); *C07F 9/6561* (2013.01); *C07F 9/65583* (2013.01); *C07F 9/657181* (2013.01)

(58) Field of Classification Search
CPC ..... C07F 9/65742; C07F 9/60; C07F 9/65583
USPC ........................................................ 546/21
See application file for complete search history.

(56) References Cited

U.S. PATENT DOCUMENTS

| | | | |
|---|---|---|---|
| 3,524,846 A | 8/1970 | Moffatt | |
| 6,011,021 A | 1/2000 | Slusher et al. | |

FOREIGN PATENT DOCUMENTS

| | | |
|---|---|---|
| WO | 2011125911 A1 | 10/2011 |
| WO | 2014043380 A1 | 3/2014 |

OTHER PUBLICATIONS

1st Office Action issued in EA20169204, English.
EESR issued in EP15777566.9.
Hong et al: [(4-Hydroxyl-benzo[4,5]thieno[3,2-c]pyridine-3-carbonyl)-amino]-acetic acid derivatives; HIF prolyl 4-hydroxylase inhibitors as oral erythropoietin secretagogues, Bioorganic & Medicinal Chemistry Letters, vol. 23, No. 21, Nov. 1, 2013, pp. 5953-5957.
Banerji B et al: The inhibition of factor inhibiting hypoxia-inducible factor (FIH) by ß-oxocarboxylic acids, Chemical Communications, No. 43, Oct. 4, 2005, pp. 5438-5440.
Mitrofanov, A. et al. "Palladium-Catalyzed Synthesis of Mono-and Diphosphorylated 1,10-Phenanthorlines", Synthesis, No. 44, Oct. 5, 2012 (Oct. 5, 2012, 3805-3810).
Alcolado, R. et al."Pathogenesis of Liver Fibrosis", Clinical Science, 1997, 92(2): 103.
Myllyharju, J., et al. "Prolyl 4-hydroxylases, the key enzymes of collagen biosynthesis", Matrix Biology, 2003, 22 (1): 15-24. accepted Jan. 2, 2003.
Stuart, Katherine A., et al."The C282Y mutation in the haemochromatosis gene (HFE) and hepatitis C virus infection are independent cofactors for porphyria cutanea tarda in Australian patients", Journal of Hepatology.1998; 28: 404-409. accepted Oct. 7, 1997.
Matsumura, Y., et al. "Prolyl 4-hydroxylase inhibitor (HOE 077) inhibits pig serum-induced rat liver fibrosis by preventing stellate cell activation", Journal of Hepatology, 1997, 27(1): 185-92. accepted Feb. 6, 1997.
Sakaida, I., et al. "The prolyl 4-hydroxylase inhibitor HOE 077 prevents activation of Ito cells, reducing procollagen gene expression in rat liver fibrosis induced by choline-deficient L-amino acid-defined diet", Hepatology, 1996, 23(4): 755-63. accepted Oct. 16, 1995.
Baader, E., et al. "Inhibition of prolyl 4-hydroxylase by oxalyl amino acid derivatives in vitro, in isolated microsomes and in embryonic chicken tissues", Biochemical Journal, 1994, 300(2): 525.
Böker, Klaus, et al. "Fibrosis of the liver in rats induced by bile duct ligation Effects of inhibition of prolyl4-hydroxylase", Journal of Hepatology.1991; 13(suppl.3):S35-S40.
Aoyagi, Mariko, et al. "Prolyl 4-hydroxylase inhibitor is more effective for the inhibition of proliferation than for inhibition of collagen synthesis of rat hepatic stellate cells", Hepatology Research 23 (2002) 1-6. accepted Sep. 26, 2001.
Sakaida, I., et al. "Prolyl 4-hydroxylase inhibitor (HOE 077) prevents TIMP-1 gene expression in rat liver fibrosis", Journal of Gastroenterology, 1999, 34(3): 376-7. Accepted: Dec. 18, 1998.
Nwogu, J. I., et al. "Inhibition of Collagen Synthesis With Prolyl 4-Hydroxylase Inhibitor Improves Left Ventricular Function and Alters the Pattern of Left Ventricular Dilatation After Myocardial Infarction", Circulation, 2001, 104(18): 2216. accepted Jul. 31, 2001.

(Continued)

*Primary Examiner* — Rita J Desai
(74) *Attorney, Agent, or Firm* — Harness, Dickey & Pierce, P.L.C.

(57) ABSTRACT

The present invention relates to a novel phenanthroline phosphonic acid compound and a pharmaceutical salt thereof, as well as an application of the compound and the pharmaceutical salt thereof as collagen prolyl hydroxylase inhibitors in the preparation of drugs for preventing or treating collagen prolyl-4-hydroxylase related disease.

16 Claims, 2 Drawing Sheets

(56) References Cited

OTHER PUBLICATIONS

Mammadov, E., et al. "Protective Effects of Phosphodiesterase-4-specific Inhibitor Rolipram on Acute Ischemia-reperfusion Injury in Rat Kidney", Urology, 2012, 80(6): 1390.e1-.e6. accepted: Jul. 21, 2012.
Hyvärinen, J., et al. "Deficiency of a Transmembrane Prolyl 4-Hydroxylase in the Zebrafish Leads to Basement Membrane Defects and Compromised Kidney Function", Journal of Biological Chemistry, 2010, 285(53): 42023-32. Sep. 21, 2010.
Erion, M. D., et al. "Liver-Targeted Drug Delivery Using HepDirect Prodrugs", Journal of Pharmacology and Experimental Therapeutics, 2005, 312(2): 554. accepted Aug. 31, 2004.
Reddy, K. R., et al. "Pradefovir: A Prodrug That Targets Adefovir to the Liver for the Treatment of Hepatitis B", Journal of Medicinal Chemistry, 2008, 51(3): 666-76. Published on Web Jan. 4, 2008.
Elhaddadi, M., et al. "A Convenient Synthesis of Alkyl and Dialkyl 1-Benzyloxyamino Alkyl Phosphonates and Phosphinates", Phosphorus, Sulfur, and Silicon and the Related Elements, 1990, 54(1-4): 143-50. final form Mar. 15, 1990.
Slavica, M., et al. "Synthesis and Biological Activities of a New Set of Irreversibly Acting 2-(4'-Isothiocyanatobenzyl) imidazoline Analogs in Rat Thoracic Aorta", Journal of Medicinal Chemistry, 1994, 37(12): 1874-81. Abstracts, May 15, 1994.
Starrett, J. E., et al. "Synthesis, Oral Bioavailability Determination, and in vitro Evaluation of Prodrugs of the Antiviral Agent 9[2-(Phosphonomethoxy)ethyl]adenine (PMEA)", Journal of Medicinal Chemistry, 1994, 37(12): 1857-64. May 1, 1994.
Bhongle, N. N., et al. "Expedient and High-Yield Synthesis of Alkylphos-Phonyl Bichlorides Under Mild, Neutral Conditions: Reaction of Bis(Trimethylsilyl)Alkyl Phosphonates with Oxalyl Chloride/Dimethylformamide", Synthetic Communications, 1987, 17(9): 1071-6.
Campbell, D. A., et al. "The synthesis of phosphonate esters; an extension of the Mitsunobu reaction", The Journal of Organic Chemistry, 1992, 57(23): 6331-5.
Muscio, Jr., Oliver J., et al. "Hydrolyses of 2- and 4-Fluor0 N-Heterocycles. 3.' Nucleophilic Catalysis by Buffer Bases in the General Acid Catalyzed Hydrolysis of 4-Fluoroquinaldine", J. Org. Chem. 1989,54, 166-171, Aug. 10, 1988.
Hauser, Charles R., et al. "Relative Ease of Cyclization of 2-, 3-, and 4-Aminopyr-idine Derivatives. Synthesis of Naphthyridines" [Contribution From the Department of Chemistry of Duke University], Jun. 1, 1960.
Kijrungphaiboon, Woranun, et al. "Cl 3 CCN/PPh 3 and CBr 4 /PPh 3 : two efficient reagent systems for the preparation of N-heteroaromatic halides",Tetrahedron Letters 53 (2012) 674-677, Nov. 25, 2011.
Chemical Research Department, et al. "The Reactions of Phosphonic Acid Esters with Acid Chlorides, 4 Very Mild Hydrolytic Route", Jun. 14, 1963.
Blackburn, G. Michael, et al. "Specific Dealkylation of Phosphonate Esters using Iodotrimethylsilane", J.C.S. Chem. Comm.,1978, Jun. 23, 1978.
Elliott, R. L., et al. "Synthesis and Biological Evaluation of Phosphonamidate Peptide Inhibitors of Enkephalinase and Angiotensin-Converting Enzyme", J. Med. Chem. 1985, 28, 1208-1216, Nov. 7, 1984.
Baddiley, J., et al., Nature, 1953, 171: 76.

Shono, T., et al. "Electroorganic chemistry. 39. Electroreductive elimination of phenolic hydroxyl groups and a new synthesis of olivetol", The Journal of Organic Chemistry, 1979, 44(25): 4508-11.
Gupta, Amar, et al. "An Improved Synthesis of Vinylic Phosphonates from Ketones", Synthetic Communications, 1 0 ( 4 ) , 299-304 (1980),1980.
Erion, M. D., et al. "Design, Synthesis, and Characterization of a Series of Cytochrome P450 3A-Activated Prodrugs (HepDirect Prodrugs) Useful for Targeting Phosph(on)ate-Based Drugs to the Liver", Journal of the American Chemical Society, 2004, 126(16): 5154-63.
Gorres, Kelly L., et al. "Prolyl 4-hydroxylase"Critical Reviews in Biochemistry and Molecular Biology 2010,45,106, Apr. 1, 2011.
Stuart, Katherine A., et al."The C282Y mutation in the haemochromatosis gene (HFE) and hepatitis", Journal of Hepatology 1998; 28: 404-409, Oct. 7, 1977.
Hoffmann, Maria. "A Simple,Efficient Synthesis of Dibenzyl and Di-p-nitrobenzyl1-Hydroxyalkanephosphonates", University of British Columbia. Copyrighted material, Apr. 1, 1987.
Stowell, Michael H. B, et al. "The mild preparation of synthetically useful phosphonic dichlorides: Application to the synthesis of cyclic phosphonic diesters and diamides Michael H.B. Stowell, Joseph M. Ueland, Ronald W. McClard", Tetrahedron Lett.,vol. 31, No. 23, pp. 3261-3262,1990, Mar. 20, 1990.
Quast, Hemlut, et al. "Heruntergeladen National University of Singapore.Urhberrechtlich geschutzt", Synthesis 1974, 490, Apr. 4, 1974.
Still, W. Clark, et al. "Direct Symthesis of Z-Umsaturated Esters.A Useful Modification of the Hormer-Emmons Olefimation", Tetrahedron Lett.1983, 24, 4405, Jul. 11, 1983.
Paquette, Leo A., et al. "Comprehensive Organic Transformations", Von R. C. Larock. VCH Publishers, Inc., New York VCH Verlagsgesellschaft, Weinheim 1989. Larock, Comprehensive organic transformations, VCH, New York, 1989,1989.
Alexander Petr, et al. "Preparation of 9-(2-Phosphonomethoxyethyl)Adenine Esters as Potential Prodrugs", Collect. Czech. Chem. Commun. 59:1853 (1994), Nov. 10, 1993.
Casara, Patrick J., et al. "Synthesis of acid stable 5'-o-fluoromethyl phosphonates of nucleosides. Evaluation as inhibitors of reverse transcriptase." Bioorg. Med. Chem. Lett. 2:145-148 (1992), Nov. 15, 1991.
Ohashi, Kinji, et al. "Synthesis of phosphonosphingoglycolipid found in marine snail turbo comutus", Tetrahedron Letters, vol. 29, No. 10, pp. 1189-1192,198, Dec. 21, 1988.
Campagne, Jean-Marc, et al. "Synthesis of Mixed Phosphonate Diester Analogues of Dipeptides using BOP or JyBOP Reagents", Teuahedron Letters. vol. 34, No. 42. pp. 6743-6744.1993, Aug. 31, 1993.
Mckenna, Charles E., et al. "The facile dealkylation of phosphonic acid dialkyl esters by bromotrimethylsilane", Tetrahedron Letters No. 2, pp. 155-158, 1977, Oct. 11, 1976.
Pelchowicz, Zvi. "Organic Phosphorus Compounds. Part I. The Reaction of Dialkyl Methylphosphonates and Methylphosphonothionates with In-organic Acid Chlorides." Pelchowiczet al., J. Chem. Soc., 1961, 238, Jan. 1, 1961.
Loczak, Barbara, et al. "ChemInform Abstract: Transesterification of Diphenyl Phosphonates Using the Potassium Fluoride/Crown Ether/Alcohol System. Part 2. The Use of Diphenyl 1-Aminoalkanephosphonates in Phosphonopeptide Synthesis", Lejczak, et al., Synthesis, 1982, 412, Nov. 13, 1981.
Baddiley, J. et al. "Structure of Coenzyme A.", Nature, 1953, 171: 76, Jan. 10, 1953.

PHENANTHROLINE PHOSPHONIC ACID DERIVATIVE AND PREPARATION METHOD THEREFOR AND APPLICATION THEREOF

CROSS-REFERENCE TO RELATED APPLICATIONS

This application is a National Stage of International Application No. PCT/CN2015/076273, filed Apr. 10, 2015 and published in Chinese as WO 2015/154716 on Oct. 15, 2015. This application claims priority to Chinese Application No. 201410142608.8, filed on Apr. 10, 2014. The entire disclosures of the above applications are incorporated herein by reference.

FIELD OF INVENTION

The present invention relates to pharmaceutical field, specially a novel phenanthroline phosphonic acid compound and a pharmaceutical salt thereof, preparation of the compound, as well as an application of the compound and the pharmaceutical salt thereof as collagen prolyl-4-hydroxylase inhibitors in the preparation of drugs for preventing or treating collagen prolyl-4-hydroxylase related disease.

BACKGROUND

The following description of the background of the invention is provided to aid in understanding the invention, but is not admitted to be, or to describe, prior art to the invention. All cited publications are incorporated by reference in their entirety.

The foundation of hepatic fibrosis is that excess collagen (especially collagen I) is synthesized (*Clin. Sci.* 1997, 92, 103) by liver which deposits on extracellular matrix (EXM). The biosynthesis of collagen includes series of post-translational modification of procollagen. Five enzymes, 3 collagen hydroxylases and 2 collagen glycosyltransferases, are involved in this process. Among these hydroxylases, prolyl-4-hydroxylase (P4H) is a tetramer of 2 α subunits (P4Hα1, P4Hα2) and 2 β subunits. β Subunit is disulfide isomerase, and the main parts having catalytic effect locate in β Subunit, and the major role of α subunit is deciding the activity of the enzyme. Prolyl-4-hydroxylase is the rate limiting enzyme in the synthesis of 21 different collagen (*Critical Reviews in Biochemistry and Molecular Biology* 2010, 45, 106). P4H locates in the endoplasmic reticulum, and catalyzes the formation of 4-hydroxyproline, from the proline residue on X-Pro-Gly sequence, in the presence of $Fe^{2+}$, $O_2$, 2-oxoglutarate and ascorbate.

P4H hydroxylate proline to 4-hydorxyproline (4-HYP) in certain positions of the procollagen, thus enhances the stability of collagen by forming triple helixes under physiological circumstances. Conversely, with less 4-HYP content, the collagen is unable to form stable triple helixes structure and degrades (*Matrix Biol.* 2003, 22, 15). Therefore, inhibition of P4H activity is widely accepted as a valid method for controlling excess collagen synthesis (fibrosis). (*Hepatol.* 1998, 28, 404). Several small molecule P4H inhibitors were verified to be effective in preventing collagen synthesis in vitro and in vivo (*J. Hepatol.* 1997, 27, 185; *Hepatol.* 1996, 23, 755; *Hepatol.* 1998, 28, 404; *Biochem. J.* 1994, 300, 525; *J. Hepatol.* 1991, 13, S35). For example, P4H inhibitor HOE077 inhibits expression of procollagen mRNA and reduces hepatic stellate cells proliferation (*Hepatol. Res.* 2002, 23, 1; *J. Hepatol.* 1997, 27, 185), also inhibits activation of hepatic stellate cells (*Hepatol.* 1996, 23, 755). The inhibitory effect of HOE077 on procollagen gene and protein was dose-dependent, but no effect on the synthesis of total protein of cell was observed. The inhibitory effect of HOE077 is possibly due to the inhibition of the expression of TIMP gene to expedite collagen degradation process (*J. Gastroenterol.* 1999, 34, 376). Several P4H inhibitors showed anti-fibrotic effects in various animal liver fibrosis models ($CO_4$, TAA etc.). (*Hepatol.* 1998, 28, 404; *Hepatol.* 1996, 23, 755; *J. Hepatol.* 1997, 27, 185). Another P4H inhibitor FG-041 (1,4-dihydrophenanthrol-4-one-3-carboxylic acid) was reported to prevent myocardial infarction in animal experiment (*Circulation* 2001, 104, 2216). P4H inhibitors were also reported to prevent bladder block (*Urology* 2012, 80, 1390).

P4H exists everywhere in body. Thus, P4H inhibitors is targeted-delivered to diseased organ while the other normal organ don't be influenced, is the key to successful development of safe and effective P4H inhibitors. In 1990s, HOECHST (which is france sanofi now) firstly developed HOE077 to treat liver cirrhosis (*Hepatol.* 1996, 23, 755; *J. Hepatol.* 1997, 27, 185). Preclinical experiments showed promising results though severe side effects (cataract) were observed in clinical trials. It is reported that inhibition of collagen synthesis could seriously influence the function of organ, such as eyes and kidneys (*J. Biol. Chem.* 2010, 285, 42023). Collagen synthesis widely exists in cellular matrix, therefore, the suppression of collagen synthesis of organ cell matrix results in the effusion of macromolecules, which cause the change of the organ function. Thus, the key to developing the P4H inhibitors used to treat organ fibrosis (such as liver fibrosis) is how to deliver the P4H inhibitors to specified organ. Prodrugs have been widely used in targeted therapeutic areas (*J. Pharmacol. Exp. Ther.* 2005, 312, 554). 1,3-Propane diols could form cyclic phosphonate esters with phosphonic acids, which were reported liver targeting (*J. Med. Chem.* 2008, 51, 666). The liver prodrug-delivery which the present invention adopts is to modify the active component of the drug to inactive prodrug. The prodrug may only be metabolized under the catalysis of liver-specific enzymes, for example, cytochrome P450, to release the active component in liver, therefor the active component produce effect in liver.

Content of the Present Invention

The purpose of the present invention is to provide a novel phenantholine phosphonic acid compound and the pharmaceutical salt thereof. The another purpose of the present invention is to provide a preparation of the compound and the pharmaceutical salt thereof. The another purpose of the present invention is to provide an application of the compound and the pharmaceutical salt thereof as collagen prolyl-4-hydroxylase inhibitors in the preparation of drugs for preventing or treating collagen prolyl-4-hydroxylase related disease.

In one aspect, the present invention provides compounds of Formula I or Formula II, and pharmaceutically acceptable salts thereof:

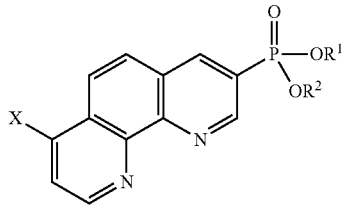

Formula I

-continued

Formula II

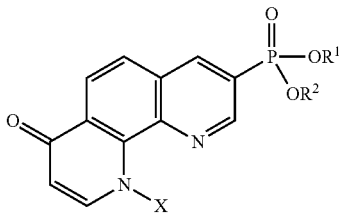

Wherein, in Formula I:
X is —Cl or —OR$^3$; R$^3$ is —H, —C(O)—(C$_1$-C$_6$ alkyl), —PO(OH)$_2$ or —CH$_2$OPO(OH)$_2$;
Each of R$^1$ and R$^2$ can be independently selected from H, C$_1$-C$_6$ alkyl, —CH$_2$OCO—(C$_1$-C$_6$ alkyl) and CH$_2$OCOO—(C$_1$-C$_6$ alkyl); or R$^1$ and R$^2$ join to form a group having the formula:

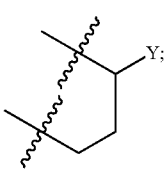

Wherein Y is aryl or heteroaryl;
In one aspect, X could be selected from —Cl, and —OR$^3$, R$^3$ is —H, —C(O)—(C$_1$-C$_6$ alkyl), —PO(OH)$_2$ or —CH$_2$OPO(OH)$_2$;
In another aspect, each of R$^1$ and R$^2$ could be independently selected from H, C$_1$-C$_6$ alkyl, —CH$_2$OCO—(C$_1$-C$_6$ alkyl) and —CH$_2$OCOO—(C$_1$-C$_6$ alkyl); or R$^1$ and R$^2$ join to form a group having the formula:

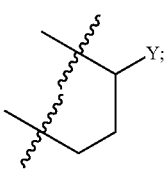

Wherein Y is aryl, heteroaryl;
Wherein, in Formula II:
Z is —H or —CH$_2$OPO(OH)$_2$; each of R$^1$ and R$^2$ is independently selected from H, C$_1$-C$_6$ alkyl, —CH$_2$OCO—(C$_1$-C$_6$ alkyl) and —CH$_2$OCOO—(C$_1$-C$_6$ alkyl); or R$^1$ and R$^2$ join to form a group having the formula:

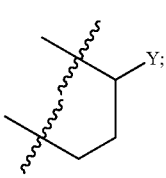

Wherein Y is aryl or heteroaryl.
In one aspect, Z could be selected from —H, and CH$_2$OPO(OH)$_2$;
In another aspect, each of R$^1$ and R$^2$ can be independently selected from H, C$_1$-C$_6$ alkyl, —CH$_2$OCO—(C$_1$-C$_6$ alkyl) and —CH$_2$OCOO—(C$_1$-C$_6$ alkyl); or R$^1$ and R$^2$ join to form a group having the formula:

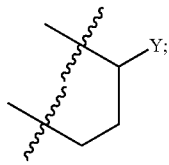

Wherein Y is aryl, heteroaryl.
In a preferred embodiment, the compound have the following formula:

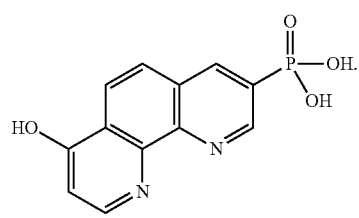 [SMILES: O=P(O)(O)c1cnc2c(ccc3c(O)ccnc32)c1]

In another preferred embodiment, the compound have the following formula:

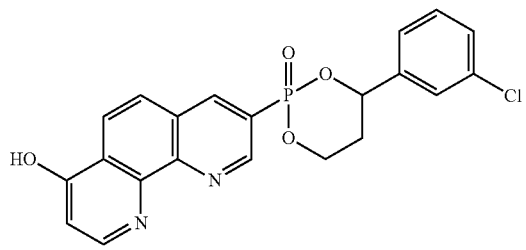 [SMILES: O=P1(c2cnc3c(ccc4c(O)ccnc43)c2)OCCC(c2cccc(Cl)c2)O1]

In another preferred embodiment, the compound have the following formula:

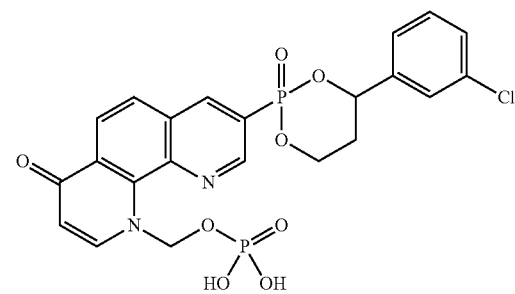 [SMILES: O=c1ccn(COP(=O)(O)O)c2c1ccc1cc(P3(=O)OCCC(c4cccc(Cl)c4)O3)cnc12]

In the second aspect, the present invention provides the method of preparing the phenantholine phosphonic acid compound and the pharmaceutical salt thereof.

In the third aspect, the present invention provides an application of the phenantholine phosphonic acid compound and the pharmaceutical salt thereof as collagen prolyl-4-hydroxylase inhibitors in the preparation of drugs for preventing or treating collagen prolyl-4-hydroxylase related disease.

The present invention provides an application of the compounds of Formula I or Formula II or the pharmaceutical salt thereof in the preparation of drugs for preventing or treating collagen prolyl-4-hydroxylase related disease.

The present invention provides an application of the compounds of Formula I or Formula II, or the in vivo metabolite thereof, or the pharmaceutical salt thereof used as collagen prolyl-4-hydroxylase inhibitors.

The present invention could protect liver function by administering to a patient with chronic liver injuries a therapeutically effective amount of the compound of Formula I and Formula II, or pharmaceutically acceptable salts thereof.

The present invention could prevent and treat liver fibrosis by administering to a patient with chronic liver injuries a therapeutically effective amount of the compound of Formula I and Formula II, or pharmaceutically acceptable salts thereof.

The present invention could prevent liver fibrosis by administering to a patient at risk for developing diabetes a therapeutically effective amount of the compound of Formula I and Formula II, or pharmaceutically acceptable salts thereof.

DETAILED DESCRIPTION OF THE PREFERRED EMBODIMENT

Definitions of Terms

Figure 1:
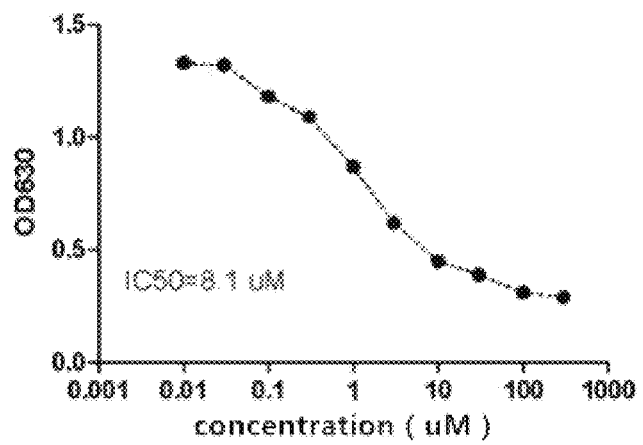
FIG. 1. The IC50 of Compound 9c against P4H enzyme

In accordance with the present invention and as used herein, the following terms are defined with the following meanings, unless explicitly stated otherwise.

The term "alkyl" refers to saturated aliphatic groups including straight-chain, branched chain and cyclic groups, up to and including 20 carbon atoms. Suitable alkyl groups include methyl, ethyl, n-propyl, isopropyl, and cyclopropyl. The alkyl may be optionally substituted with 1-3 substituents.

The term "aryl" refers to aromatic groups which have 5-14 ring atoms and at least one ring having a conjugated pi electron system and includes carbocyclic aryl, heterocyclic aryl, fused aryl and biaryl aryl, all of which may be optionally substituted. The aryl may be optionally substituted with 1-6 substituents.

Heterocyclic aryl or heteroaryl groups are groups which have 5-14 ring atoms wherein 1 to 4 heteroatoms are ring atoms in the aromatic ring and the remainder of the ring atoms being carbon atoms. Suitable heteroatoms include oxygen, sulfur, nitrogen, and selenium. Suitable heteroarylgroups include furanyl, thienyl, pyridyl, pyrrolyl, N-lower alkyl pyrrolyl, pyridyl-N-oxide, pyrimidyl, pyrazinyl, imidazolyl, and the like, all optionally substituted.

The term "optionally substituted" or "substituted" refers to the groups substituted by one to four substituents, independently selected from lower alkyl, lower aryl, lower aralkyl, lower cyclic alkyl, lower heterocycloalkyl, hydroxy, lower alkoxy, lower aryloxy, perhaloalkoxy, aralkoxy, lower heteroaryl, lower heteroaryloxy, lower heteroarylalkyl, lower heteroaralkoxy, azido, amino, halo, lower alkylthio, oxo, lower acylalkyl, lower carboxy esters, carboxyl, carboxamido, nitro, lower acyloxy, lower aminoalkyl, lower alkylaminoaryl, lower alkylaryl, lower alkylaminoalkyl, lower alkoxyaryl, lower arylamino, lower aralkylamino, sulfonyl, lower carboxamidoalkylaryl, lower carboxamidoaryl, lower hydroxyalkyl, lower haloalkyl, lower alkylaminoalkylcarboxy, lower aminocarboxamidoalkyl, cyano, lower alkoxyalkyl, lower perhaloalkyl, and lower arylalkyloxyalkyl.

"Substituted aryl" and "substituted heteroaryl" refers to aryl and heteroarylgroups substituted with 1-6 substituents. These substituents are selected from lower alkyl, lower alkoxy, lower perhaloalkyl, halo, hydroxy, and amino.

The term "halogen" or "halo" refers to —F, —Cl, —Br and —I.

The phrase "therapeutically effective amount" means an amount of the compound or a combination of compounds needed to ameliorates, attenuates, eliminates or prevents, modifies, delays one or more of the symptoms of a particular disease The term "pharmaceutically acceptable salt" refers to the salts generated by mixing the compounds of Formula I or Formula II and the prodrug thereof with an organic or inorganic acid or base. Suitable acids include acetic acid, adipic acid, benzenesulfonic acid, (+)-7,7-dimethyl-2-oxo-bicyclo[2.2.1]heptane-1-methanesulfonic acid, citric acid, 1,2-ethanedisulfonic acid, dodecyl sulfonic acid, fumaric acid, glucoheptonic acid, gluconic acid, glucuronic acid, hippuric acid, hydrochloride hemiethanolic acid, HBr, HCl, HI, 2-hydroxyethanesulfonic acid, lactic acid, lactobionic acid, maleic acid, methanesulfonic acid, methylbromide acid, methyl sulfuric acid, 2-naphthalenesulfonic acid, nitric acid, oleic acid, 4,4'-methylenebis [3-hydroxy-2-naphthalenecarboxylic acid], phosphoric acid, polygalacturonic acid, stearic acid, succinic acid, sulfuric acid, sulfosalicylic acid, tannic acid, tartaric acid, terphthalic acid, and p-toluenesulfonic acid. The salt generated by mixing with suitable base is sodium salt, potassium salt, calcium salt, magnesium salt, lithium salt, cesium salt, amino acid salt.

The term "patient" refers to a male or female mammal animal being treated, such as a dog, a cat, a cow, a horse, a sheep, and a human.

The term "prodrug" as used herein refers to any compound that when administered to a biological system generates a biologically active compound as a result of spontaneous chemical reaction(s), enzyme catalyzed chemical reaction(s), and/or metabolic chemical reaction(s), or a combination of each. Standard prodrugs are formed using groups attached to functionality, e.g. HO—, HS—, HOOC—, $R_2N$—, associated with the drug, that cleave in vivo. Standard prodrugs include but are not limited to carboxylate esters where the group is alkyl, aryl, aralkyl, acyloxyalkyl, alkoxycarbonyloxyalkyl, as well as acyl, alkoxycarbonyl, aminocarbonyl, phosphate or sulfate which attached to hydroxyl, thiol and amines. The groups illustrated are exemplary, not exhaustive, and one skilled in the art could prepare other known varieties of prodrugs. Such prodrugs of the compounds of Formula I and II fall within this scope. Prodrugs must undergo some form of a chemical transformation to produce the compound that is biologically active or is a precursor of the biologically active compound. In some cases, the prodrug is biologically active, usually less than the drug itself, and serves to improve drug efficacy or safety through improved oral bioavailability, pharmacodynamic half-life, etc. Prodrug forms of compounds may be utilized, for example, to improve bioavailability, improve subject acceptability by masking or reducing unpleasant characteristics such as bitter taste or gastrointestinal irritability, alter solubility for intravenous use, provide for prolonged or sustained release or delivery, improve ease of formulation, or provide site-specific delivery of the compound. Prodrugs are described in The Organic Chemistry of Drug Design and Drug Action, by Richard B. Silverman, Academic Press, San Diego, 1992. Chapter 8: "Prodrugs and Drug delivery Systems" pp. 352-401; Design of Prodrugs, edited by H. Bundgaard, Elsevier Science, Amsterdam, 1985; Design of Biopharmaceutical Properties through Prodrugs and Analogs, Ed. by E. B. Roche, American Pharmaceutical Association, Washington, 1977; and Drug Delivery Systems, ed. by R. L. Juliano, Oxford Univ. Press, Oxford, 1980.

The term "percent enantiomeric excess (% ee)" refers to optical purity. It is obtained by the following formula:

$$\frac{[R] - [S]}{[R] + [S]} \times 100 = \% \ R - \% \ S$$

wherein [R] represents the amount of the R isomer, and [S] represents the amount of the S isomer. This formula provides the % ee when R is the dominant isomer.

The terms "treating" or "treatment" a disease, includes preventing the disease from occurring (prophylactic treatment), inhibiting the disease (slowing or arresting its development), providing relief from the symptoms or side-effects of the disease (including palliative treatment), and relieving the disease (causing regression of the disease).

The formulations of the compound of the present patent:

Compounds of the invention are administered in a total daily dose of 0.01 to 2500 mg. In one aspect, the range is about 5 mg to about 500 mg. The dose may be administered in as many divided doses as is convenient.

Compounds of this invention when used in combination with other agents may be administered as a daily dose or an appropriate fraction of the daily dose (e.g., bid). The compounds of this invention may be used as a part of a multidrug regimen, also known as combination or 'cocktail' therapy, wherein, multiple agents may be administered together, may be administered separately at the same time or at different intervals, or administered sequentially. The compounds of this invention may be administered after a course of treatment by another agent, during a course of therapy with another agent, administered as part of a therapeutic regimen, or may be administered prior to therapy by another agent in a treatment program.

For achieving the purpose of treatment, the compounds of this invention may be administered by a variety of means including orally, parenterally, by inhalation spray, topically, or rectally in formulations containing pharmaceutically acceptable carriers, adjuvants and vehicles. The term parenteral as used here includes subcutaneous, intravenous, intramuscular, and intraarterial injections with a variety of infusion techniques. Intraarterial and intravenous injection as used herein includes administration through catheters. Intravenous administration is generally preferred. Pharmaceutically acceptable salts include sodium salt, potassium salt, calcium salt, magnesium salt, lithium salt, cesium salt, amino acid salt, acetate, adipate, besylate, bromide, camsylate, hydrochloride, citrate, edisylate, estolate, fumarate, gluceptate, gluconate, glucoranate, hippurate, hyclate, bromide, chloride, iodide, isethionate, lactate, lactobionate, maleate, mesylate, methylbromide, methylsulfate, napsylate, nitrate, oleate, palmoate, phosphate, polygalacturonate, stearate, succinate, sulfate, sulfo salicylate, tannate, tartrate, terphthalate, tosylate, and triethiodide.

The active ingredient of drug have different forms for different method of administration. For example, when used for oral use, tablets, troches, lozenges, aqueous or oil suspensions, dispersible powders or granules, emulsions, hard or soft capsules, syrups or elixirs may be prepared. The method of preparing oral preparation could refer to the manufacturing process of known medicine. In order to provide a palatable preparation, the preparation may contain one or more agents including sweetening agents, flavoring agents, coloring agents and preserving agents. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be in the form of hard gelatin capsules in which the active ingredient is mixed with an inert solid diluent, for example calcium phosphate or kaolin, or as soft gelatin capsules in which the active ingredient is mixed with water or an oil medium, such as peanut oil, liquid paraffin or olive oil.

The active ingredients of the invention may be also mixed with excipients suitable for industrial manufacture to produce aqueous suspensions. Such excipients include suspending agent, such as sodium carboxymethylcellulose, methylcellulose, ethylcellulose, hydroxypropylcellulose, hydroxypropyl methylcellulose, sodium alginate, polyvinylpyrrolidone, gum tragacanth and gum acacia; dispersing or wetting agents, such as a natural phosphatide (e.g., lecithin), condensation products of alkylene oxides with fatty acids (e.g., polyoxyethylene stearate), condensation products of ethylene oxides with long chain aliphatic alcohols (e.g., heptadecyl ethyleneoxy ethanol), condensation products of ethylene oxide with a partial ester derived from fatty acids and hexitol anhydrides (e.g., polyoxyethylene sorbitan monooleate). The aqueous suspension may also contain one or more preservatives such as ethyl or n-propyl p-hydroxy-benzoate, coloring agents, flavoring agents and sweetening agents, such as sucrose and saccharin.

Oil suspensions may be formulated by suspending the active ingredient in a vegetable oil (such as arachis oil, olive oil, sesame oil or coconut oil), or in a mineral oil (such as liquid paraffin). The oral suspensions may also contain a thickening agent (such as beeswax, hard paraffin or cetyl alcohol). Sweetening agents such as those set forth above, and flavoring agents may be added to provide a palatable oral preparation. These compositions may be preserved by the addition of an antioxidant such as ascorbic acid. Dispersible powders and granules of the invention is suitable for preparation of an aqueous suspension by the addition of water generally contain the the active ingredient together with a dispersing or wetting agent, suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions of the invention may also be in the form of oil-in-water emulsions. The oily phase may be a vegetable oil, such as olive oil and arachis oil, a mineral oil, such as liquid paraffin, or a mixture of these. Suitable emulsifying agents include naturally-occurring gums, such as gum acacia and gum tragacanth, naturally-occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion may also contain sweetening and flavoring agents.

Syrups and elixirs may be formulated with sweetening agents, such as glycerol, sorbitol or sucrose. Such formulations may also contain a demulcent, preservative, flavoring or coloring agent.

The pharmaceutical compositions of the invention may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a solution or suspension which is prepared by non-toxic injectable diluent or solvent, such as preparing lyophilized powder and dissolving in 1,3-butane-diol. The acceptable vehicles and solvents may be water, Ringer's solution and isotonic sodium chloride solution. In addition, sterile fixed oils may conventionally be employed as a solvent or suspending medium. Any bland fixed oil may be employed including synthetic mono- or di-glycerides. In addition, fatty acids such as oleic acid may likewise be used in the injectable preparation.

The amount of active ingredient that may be combined with the carrier material to produce a single dosage form will vary depending upon the host treated and the particular mode of administration. For example, a time-release formulation intended for oral administration to humans may contain 20 to 2000 μmol (approximately 10 to 1000 mg) active ingredient and appropriate carrier material which may vary from about 5 to about 95% of the total compositions. It is preferred that the pharmaceutical composition be prepared which provides easily measurable amounts for administration. For example, an aqueous solution intended for intravenous infusion should contain from about 0.05 to about 50 μmol (approximately 0.025 to 25 mg) of the active ingredient per milliliter of solution in order that infusion of a suitable volume at a rate of about 30 mL/hr can occur.

As noted above, oral preparation may be presented as discrete units such as capsules, cachets or tablets, each containing a predetermined amount of the active ingredient; as a powder or granules; as a solution or suspension in an aqueous or non-aqueous liquid; or as an oil-in-water liquid emulsion or a water-in-oil liquid emulsion. The active ingredient may also be administered as a bolus, electuary or paste.

A tablet may be made by compression or molding, optionally with one or more accessory ingredients. Compressed tablets may be prepared by compressing in a suitable machine the active ingredient in a free flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose) surface active or dispersing agent. Molded tablets may be made by molding in a suitable machine a mixture of the powdered compound moistened with an inert liquid diluent. The tablets may optionally be coated or scored in preparing so as to provide slow or controlled release of the active ingredient therein using, for example, hydroxypropyl methylcellulose in varying proportions to provide the desired release profile. Tablets may optionally be provided with an enteric coating, to provide release in parts of the gut other than the stomach. This is particularly advantageous with the compounds of Formula I when such compounds are susceptible to acid hydrolysis.

Formulations suitable for topical administration in the mouth include pastille comprising the active ingredient in a flavored base, usually sucrose, acacia or tragacanth; pastilles comprising the active ingredient in an inert base such as gelatin, glycerin, sucrose and acacia; and mouthwashes comprising the active ingredient in a suitable liquid carrier.

Formulations for rectal administration may be presented as a suppository comprising the active compound in a suitable base comprising such as cocoa, butter or a salicylate. Formulations suitable for vaginal administration may add the active ingredient and known suitable carriers in pessaries, tampons, creams, gels, pastes, foams or spray.

Formulations suitable for parenteral administration include aqueous and non-aqueous isotonic sterile injection solutions which may contain antioxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose sealed containers, for example, ampoules and vials, and may be stored in a freeze-dried (lyophilized) condition requiring only the addition of the sterile liquid carrier, for example water for injections, immediately prior to use.

Injection solutions and suspensions may be prepared from sterile powders, granules and tablets of the kind previously described.

Formulations suitable for parenteral administration may be administered in a continuous infusion manner via an indwelling pump or via a hospital bag. The infusions may be done through a Hickman or PICC or any other means suitable for parenterally and i.v.

Preferred unit dosage formulations contains a daily dose or unit, each dose, and daily frequency.

It will be understood, however, that the specific dose level for any particular patient will depend on a variety of factors including the activity of the specific compound employed; the age, body weight, general health, sex and diet of the individual being treated; the time and route of administration; the rate of excretion; other drugs which have previously been administered; and the severity of the particular disease undergoing therapy, as is well understood by those skilled in the art.

Synthesis of the Compounds of Formula I and Formula II

The compounds in this invention may be prepared by the processes described in the following discussions, as well as relevant published literature procedures that are used by those skilled in the art. It should be understood that the following discussions are provided solely for the purpose of illustration and do not limit the invention which is defined by the claims. Typically the synthesis of the compound of Formula I includes the following general five steps (listed in reversed order): (1) Preparation of a prodrug; (2) Deprotection of a phosphonate ester; (3) Modifications of an existing quinoline; (4) Construction of a quinoline; and (5) Preparation of key precursors. The compounds of Formula II could be synthesized by the compounds of Formula I reacting with suitable groups. Protection and deprotection in the Schemes may be carried out according to the procedures generally known in the art (e.g., "Protecting Groups in Organic Synthesis," 3rd Edition, Wiley, 1999).

All stereoisomers of the compounds of the present invention are contemplated, either in admixture or in pure or substantially pure form. The compounds of the present invention can have stereogenic centers at the phosphorus atom and at any of the carbons including any of the R substituents. Consequently, compounds of Formula I can exist in enantiomeric or diastereomeric forms or in mixtures thereof. The processes for preparation can utilize racemates, enantiomers or diastereomers as starting materials. When enantiomeric or diastereomeric products are prepared, they can be separated by conventional methods. For example, chromatography or fractional crystallization can be used to separate diastereomeric mixtures, while derivatives of enantiomeric isomers can be separated via chromatography.

1) Preparation of a Prodrug

Prodrugs can be introduced at different stages of the synthesis. Most often these prodrugs are introduced at the later stage of a synthesis due to the lability of various prodrugs, while prodrugs could also be introduced at an early stage of the synthesis due to other considerations.

The compounds of Formula I could be phosphonic acids wherein both $R^1$ and $R^2$ are H, and also be in a suitably protected form. Phosphonic acids can be alkylated with electrophiles such as alkyl halides and alkyl sulfonates under nucleophilic substitution conditions to give phosphonate esters. For example, compounds of Formula I wherein W and $R^2$ are acyloxyalkyl groups can be prepared by direct alkylation of compounds of Formula I wherein both $R^1$ and $R^2$ are H with an appropriate acyloxyalkyl halide (e.g. Cl, Br, I; *Phosphorus Sulfur* 1990, 54, 143; *Synthesis* 1988, 62) in the presence of a suitable base (e.g. pyridine, TEA, diisopropylethylamine) in suitable solvents such as DMF (*J. Med. Chem.* 1994, 37, 1875). The carboxylate component of these acyloxyalkyl halides includes but is not limited to acetate, propionate, isobutyrate, pivalate, benzoate, carbonate and other carboxylates.

Reactive dichlorophosphonates can be generated from the corresponding phosphonic acids with a chlorinating agent (e.g. thionyl chloride, *J. Med. Chem.* 1994, 1857; oxalyl chloride, *Tetrahedron Lett.* 1990, 31, 3261; phosphorous pentachloride, *Synthesis* 1974, 490). Alternatively, a dichlorophosphonate can be generated from its corresponding disilyl phosphonate esters (*Synth. Commu.* 1987, 17, 1071) and dialkyl phosphonate esters (*Tetrahedron Lett.* 1983, 24, 4405; *Bull. Soc. Chim.* 1993, 130, 485). Cyclic phosphonate esters of substituted 1,3-propane diols can be synthesized by either reactions of the corresponding dichlorophosphonate with a substituted 1,3-propanediol or coupling reactions using suitable coupling reagents (e.g. DCC, EDCI, PyBOP; *Synthesis* 1988, 62).

Alternatively, these cyclic phosphonate esters of substituted 1,3-propane diols are prepared from phosphonic acids by coupling with diols under Mitsunobu reaction conditions (*Synthesis* 1 (1981); *J. Org. Chem.* 52:6331 (1992)), and other acid coupling reagents including, but not limited to, carbodiimides (*Collect. Czech. Chem. Commun.* 59:1853 (1994); *Bioorg. Med. Chem. Lett.* 2:145 (1992); *Tetrahedron Lett.* 29:1189 (1988)), and PyBOP (*Tetrahedron Lett.* 34, 6743 (1993)).

One aspect of the present invention provides methods to synthesize and isolate single isomers of prodrugs of phosphonic acids of Formula I. Because phosphorus is a stereogenic atom, formation of a prodrug with a racemic substituted-1,3-propane-diol will produce a mixture of isomers. For example, formation of a prodrug with a racemic 1-(Y)-substituted-1,3-propane diol gives a racemic mixture of cis-prodrugs and a racemic mixture of trans-prodrugs. In another aspect, the use of the enantioenriched substituted-1,3-propane diol with the R-configuration gives enantioenriched R-cis- and R-trans-prodrugs. These compounds can be separated by a combination of column chromatography and/or fractional crystallization.

Another prodrug group can be introduced for expected properties. Compounds of Formula I (X=OH) can be connected with different protecting groups on the O atom of N atom of the hydroxypyridine ring. For example, compounds of formula I ($R^3$ is carboxyl group) could be prepared from compound of formula I ($R^3$ is H) with appropriate carboxyl halide under suitable reaction conditions (*J. Org. Chem.* 1989, 54, 166); compounds of formula I (X is Cl) could be generated from compound of formula I (X is OH) with different chlorinating reagent (for example: $POCl_3$, *J. Org. Chem.* 1950, 15, 1224; $CCl_3CN$, *Tetrahedron Lett.* 2012, 53, 674) under appropriate conditions.

2) Deprotection of a Phosphonate Ester

Compounds of Formula I wherein $R^1$ is H may be prepared from phosphonate esters using known phosphate and phosphonate ester cleavage conditions. Silyl halides are generally used to cleave various phosphonate esters, and subsequent mild hydrolysis of the resulting silyl phosphonate esters give the desired phosphonic acids. When required, acid scavengers (e.g. 1,1,1,3,3,3-hexamethyldisilazane, 2,6-lutidine) can be used for the synthesis of acid labile compounds. Such silyl halides include chlorotrimethylsilane *J. Org. Chem.,* 1963, 28: 2975), and bromotrimethylsilane (*Tetrahedron Lett.,* 1977, 155), and iodotrimethylsilane (*J. Chem. Soc., Chem. Commun.,* 1978, 870). Alternately, phosphonate esters can be cleaved under strong acidic conditions (e.g. HBr or HCl: Moffatt, et al, U.S. Pat. No. 3,524,846, 1970). These esters can also be cleaved via dichlorophosphonates, prepared by treating the esters with halogenating agents (e.g. phosphorus pentachloride, thionyl chloride, $BBr_3$: Pelchowicz et al., *J. Chem. Soc.,* 1961, 238) followed by aqueous hydrolysis to give phosphonic acids. Aryl and benzyl phosphonate esters can be cleaved under hydrogenolysis conditions (Lejczak, et al., *Synthesis,* 1982, 412; Elliott, et al., *J. Med. Chem.,* 1985, 28: 1208; Baddiley, et al., *Nature,* 1953, 171: 76) or metal reduction conditions (Shafer, et al., *J. Am. Chem. Soc.,* 1977, 99: 5118). Electrochemical (Shono, et al., *J. Org. Chem.,* 1979, 44: 4508) and pyrolysis (Gupta, et al., *Synth. Commun.,* 1980, 10: 299) conditions have also been used to cleave various phosphonate esters.

(3) Synthesis of Phosphorus-Containing Phenantholines

Construction of the phenantholine core could be carried out using well-established literature methods. For example, a thermal cyclization strategy is illustrated in the following scheme.

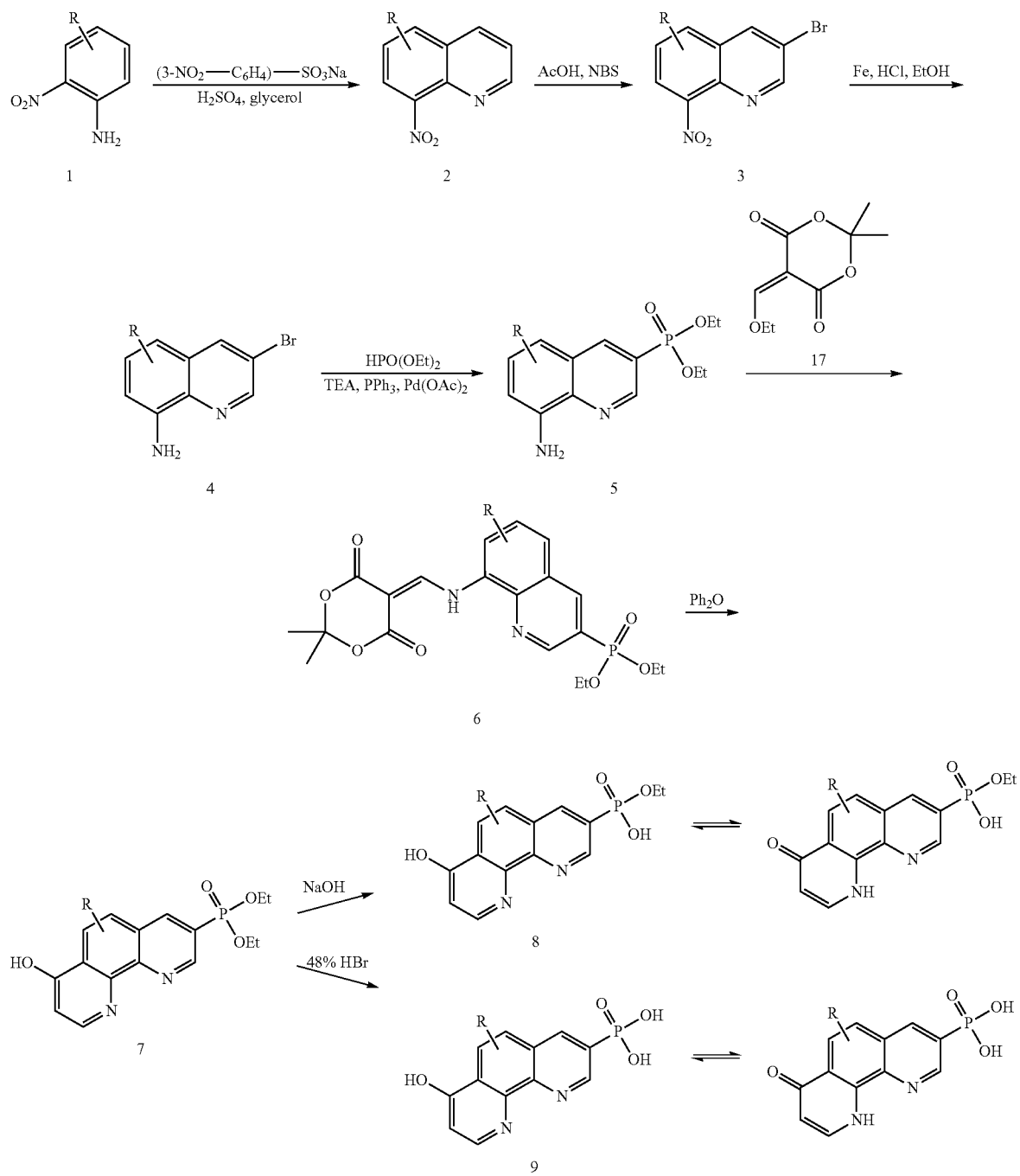

Treatment of arylamine 1 with sodium 3-nitrobenzene-sulfonate, sulfuric acid and glycerol provided quinoline 2. Bromination of quinoline 2 using NBS in acetic acid provided compound 3 which was reduced using iron to give compound 4. Phosphonylation of compound 4 gave phosphonate 5 which was treated with compound 17 and followed by a thermal cyclization reaction to provide phenantholine 7 wherein R is H (compounds of formula I wherein X is OH, $R^1=R^2=Et$). Treatment of compound 7 with sodium hydroxide provided compound 8 wherein R is H (compounds of formula I wherein X is OH, $R^1=H$, $R^2=Et$); on the other hand, treatment of compound 7 with 48% HBr provided compound 9 wherein R is H (compounds of formula I wherein X is OH, $R^1=R^2=H$). In some cases, the desired substituents are not compatible with subsequent reactions, and therefore modifications of an existing phenantholine are envisioned using conventional chemistry (Larock, *Comprehensive organic transformations*, VCH, New York, 1989; Trost, *Comprehensive organic synthesis*; Pergamon press, New York, 1991).

Prodrugs often are introduced at the later stage of a synthesis, while some prodrugs could also be introduced at an early stage of the synthesis due to other considerations. For example, the cyclic phosphonate diester prodrugs could be prepared as illustrated in the following scheme.

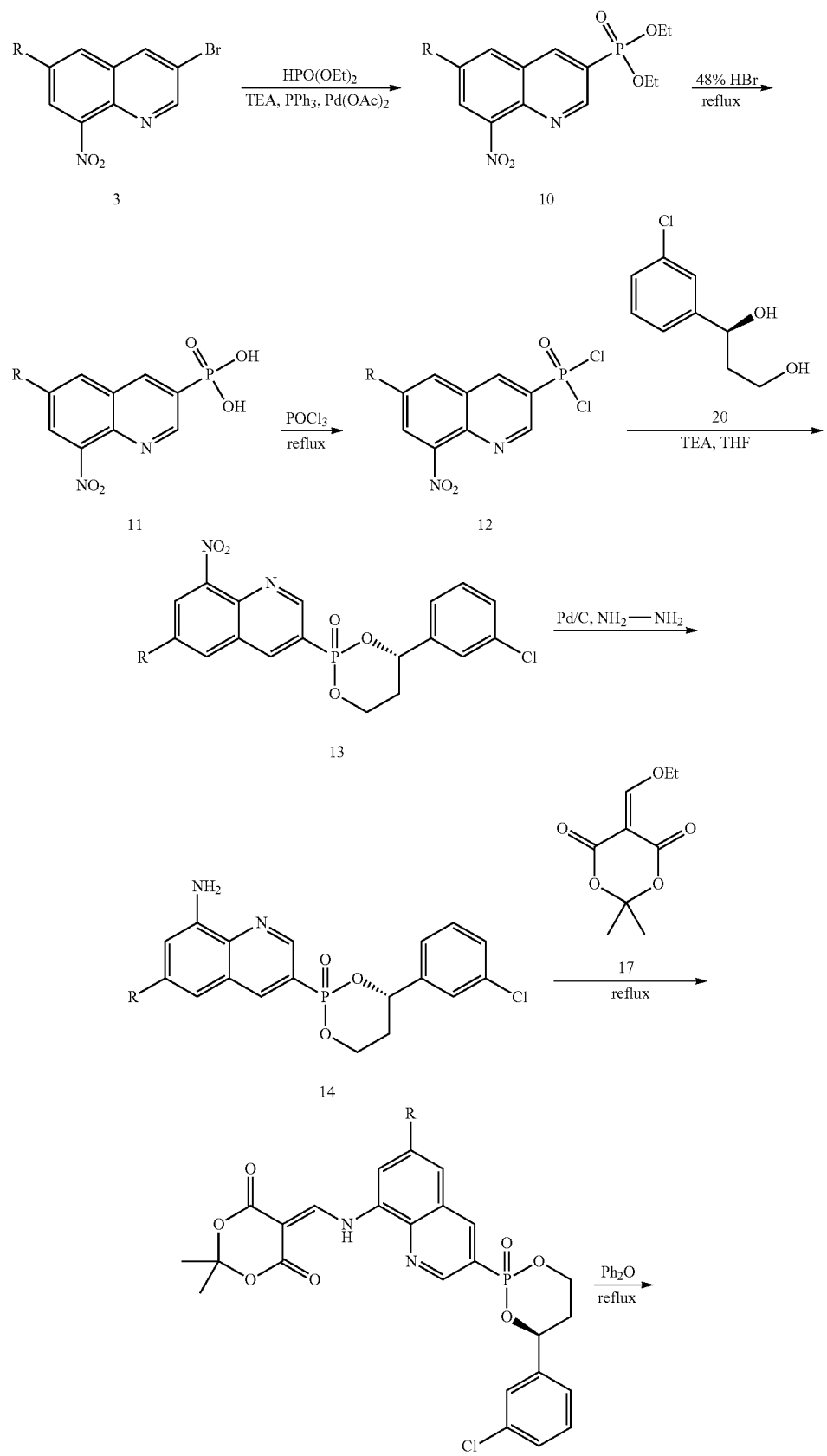

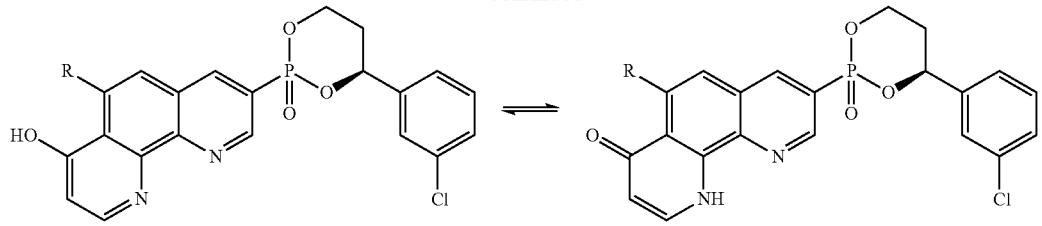

16

Phosphonylation of compound 3 gave phosphonate 10 which was deprotected using 48% HBr to give phosphonic acid 11. Treatment of compound 11 with POCl₃ gave the reactive dichlorophosphonates 12 which was immediately coupled with diol 20 (*J. Am. Chem. Soc.* 2004, 5154) to give compound 13. Reduction of the nitro group in compound 13 followed by reaction with compound 17 and then thermal ring closure to give phenantholine 16 wherein R is H (compounds of formula I wherein X is OH, $R^1$ and $R^2$ together form a cyclic group).

Another prodrug group can be introduced for expected properties. For example, compound 16c reacted with chlorophosphate under suitable base (for example: Et₃N) and catalyst (for example: 4-dimethylaminopyridine) in suitable solvent (for example: CH₂Cl₂) to yield phosphate 21. The deprotection of diethyl phosphate can be achieved by using common phosphate deprotecting reagent. For example, deprotection of phosphate 21 by trimethylsilyl bromide gave phosphoric acid 22, which can be converted to desired salt. For example, compound 22 mixed with sodium bicarbonate in water and methanol could give disodium salt 23.

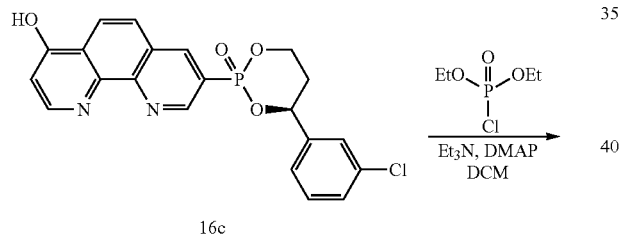

16c

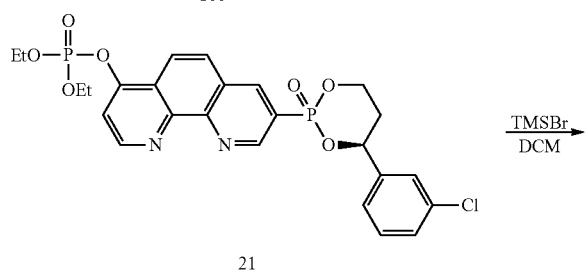

21

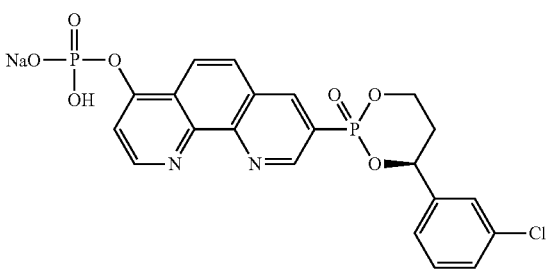

22

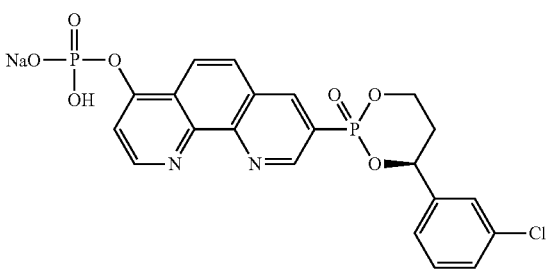

23

In another example, other types of prodrugs could be formed for different expected properties. For example, di-t-butylchloromethyl phosphate reacted with phenanthroline 16c under suitable base (for example: K₂CO₃) in suitable solvent (for example: DMSO) to afford phosphate ester 24 and 25. Common t-butyl deprotecting agent could be used to remove di-t-butyl groups. For example, deprotection of 24 and 25 with trifluoroacetic acid in dichloromethane gave phosphoric acid 26 and 27, respectively. Compound 26 and 27 could be further converted to desired salts.

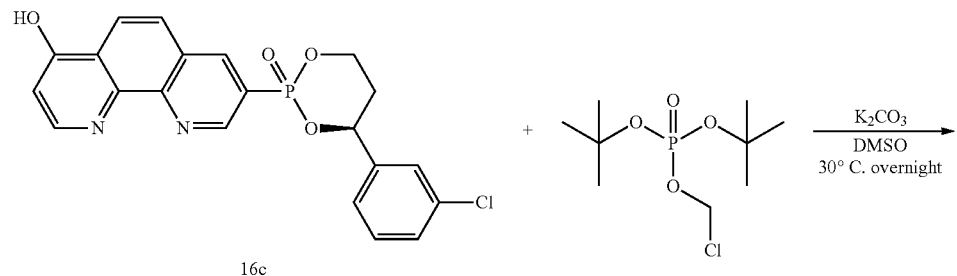

16c

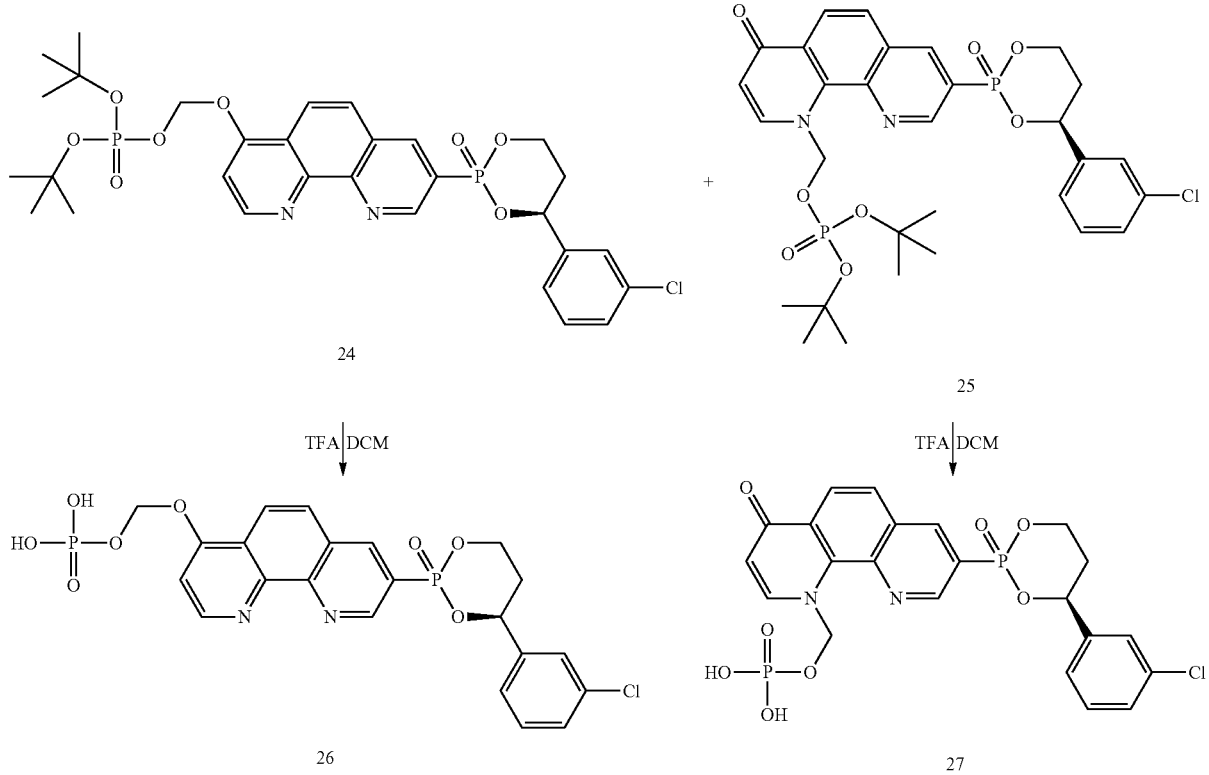

EXAMPLES

The compounds used in this invention and their preparation can be understood further by the Examples. These Examples should not however be construed as specifically limiting the invention, and variations of the compounds, now known or later developed, are considered to fall within the scope of the present invention as hereinafter claimed.

Example 1. Syntheses of Compounds

The Preparation of 8-nitroquinoline (2c)

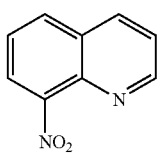

A mixture was prepared to which 47 g of $H_2SO_4$, 20 ml of $H_2O$, 23.4 g (0.104 mol) of sodium 3-nitrobenzene sulfonate, and 22 ml of glycerol were added in that order. It was warmed gently until forming a solution, and 11 g 2-nitroaniline 1c (0.08 mol) was added in portions. The mixture was refluxed for 5 h. After cooling to room temperature, the mixture was poured into 600 ml $H_2O$ under ice bath, adjusted to pH 6-7 with aqueous ammonia, and suction-filtered. The cake was dried and purified with chromatography (EA:PE=1:5). A yellow solid 2c 6.177 g was given in 44%.

1H NMR (300 MHz, CDCl3) δ 9.09 (dd, J=1.8 Hz, 4.5 Hz, 1H), 8.28 (dd, J=1.8 Hz, 8.4 Hz, 1H), 8.05 (d, J=9 Hz, 2H), 7.66-7.55 (m, 2H).

The Preparation of 3-bromo-8-nitroquinoline (3c)

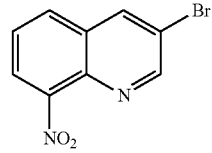

8-nitroquinoline 2c 6.177 g (35.5 mmol) was added to 110 ml of acetic acid, and then 6.651 g NBS (35.5 mmol) was added. The mixture reacted at 50° C. for 2 h. The reaction mixture was cooled and poured into 600 ml $H_2O$, and suction-filtered. The cake was dried and purified with chromatography (EA:PE=1:15) to give yellow solid 3c 2.625 g in 29%.

1H NMR (300 MHz, CDCl3) δ9.06 (d, J=2.1 Hz, 1H), 8.44 (d, J=2.4 Hz, 1H), 8.06 (d, J=7.5 Hz, 1H), 7.98 (d, J=8.1 Hz, 1H), 7.67 (t, J=7.8 Hz, 1H).

The Preparation of 3-bromoquinolin-8-amine (4c)

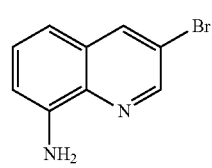

Compound 3c (13.0 g, 51.6 mmol) was added to EtOH (150 mL), and then iron powder (11.6 g, 206.4 mmol), $NH_4Cl$ (11.0 g, 206.4 mmol) was added. The resulting was refluxed for overnight. The reaction mixture was cooled and filtered through celite. The filtrate was evaporated to dryness and purified with chromatography (EA:PE=1:5). A yellow solid 4c 8.23 g was given in 72%.

1H NMR (300 MHz, CDCl3) δ 8.72 (d, J=2.1 Hz 1H), 8.21 (d, J=2.1 Hz, 1H), 7.35 (t, J=7.8 Hz, 1H), 7.05 (dd, J=1.2 Hz, 8.1 Hz, 1H), 7.61 (dd, J=1.2 Hz, 7.5 Hz, 1H), 4.98 (s, 2H).

The Preparation of Diethyl 8-aminoquinolin-3-yl phosphonate (5c)

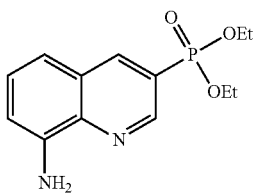

5c

Compound 4c (4.0 g, 17.9 mmol) was added to EtOH (53 mL) under N2, and then HPO(OEt)2 (3.0 mL, 23.3 mmol), TEA (3.7 mL, 26.9 mmol), Ph3P (1.27 g, 4.8 mmol) and Pd(OAc)2 (0.8 g, 3.58 mmol) was added. The resulting mixture was refluxed for overnight. The reaction mixture was cooled to room temperature and charged with H2O (100 mL), extracted with EA. The organic layers was merged, washed with brine, dried over anhydrous Na2SO4, concentrated, and purified with chromatography (EA:PE=1:1). A yellow oil 5c 1.4 g was given in 25%.

1H NMR (300 MHz, CDCl3) δ 8.98 (dd, J=1.8 Hz, 4.2 Hz, 1H), 8.59 (dd, J=2.1 Hz, 15.3 Hz, 1H), 7.38 (d, J=7.8 Hz, 1H), 7.21 (d, J=7.5 Hz, 1H), 7.01 (t, J=7.5 Hz, 1H), 4.20-4.07 (m, 4H), 1.35 (t, J=6.9 Hz, 6H)

The Preparation of Diethyl 8-((2,2-dimethyl-4,6-dioxo-1,3-dioxan-5-ylidene)methylamino)quinolin-3-yl phosphonate (6c)

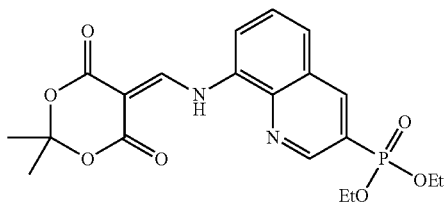

6c

Compound 5c (1.4 g, 5 mmol) was added to EtOH (40 mL) under N2, and then compound 17 was added. The reaction mixture was refluxed for overnight. The reaction mixture was cooled to room temperature, evaporated the solvent and purified with chromatography (EA:PE=1:1). A yellow solid 6c 1.125 g was given in 52%.

1H NMR (300 MHz, CDCl3) δ 12.8 (d, J=15 Hz, 1H), 9.20 (dd, J=1.8 Hz, 4.2 Hz, 1H), 8.91 (d, J=14.7 Hz, 1H), 8.74 (dd, J=1.8 Hz, 15.3 Hz 1H), 7.80-7.76 (m, 2H), 7.67 (t, J=7.8 Hz, 1H), 4.30-4.09 (m, 4H), 1.81 (s, 6H), 1.35 (t, J=6.9 Hz, 6H).

The Preparation of Diethyl 7-hydroxy-1,10-phenanthrolin-3-yl phosphonate (7c)

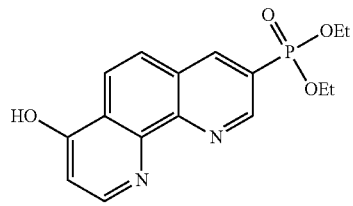

7c

Diphenyl ether was heated to boiling, compound 6c (1.1 g, 2.5 mmol) was added to rapidly. The resulting mixture was stirred for 2 min at reflux. The mixture was cooled to 100° C., poured into PE (640 mL) under stirring, suction-filtered. The cake was purified with chromatography (MeOH:DCM=1:20). A yellow solid 7c 650 mg was given in 77%.

1H NMR (300 MHz, CDCl3) δ 10.8 (s, 1H), 9.31 (dd, J=1.8 Hz, 5.1 Hz, 1H), 8.72 (dd, J=1.8 Hz, 14.7 Hz, 1H), 8.49 (d, J=8.7 Hz, 1H), 7.94 (d, J=7.5 Hz, 1H), 7.71 (d, J=9 Hz, 1H), 6.62 (d, J=7.5 Hz, 1H), 4.35-4.14 (m, 4H), 1.39 (t, J=6.9 Hz, 6H).

The Preparation of 7-hydroxy-1,10-phenanthrolin-3-yl phosphonic acid (9c)

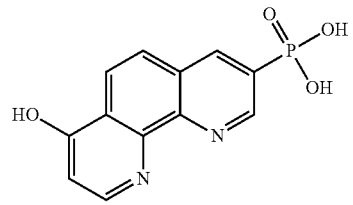

9c

Compound 7c (650 mg) was added to 48% HBr aq. The resulting mixture was refluxed for overnight. The reaction mixture was cooled to room temperature, evaporated the solvent, stirred with a small amount of water, suction-filtered, and dried. A gray solid 9c 513 mg was given in 95%.

1H NMR (300 MHz, D2O) δ 8.99 (dd, J=4.5 Hz, 1.8 Hz, 1H), 8.30 (dd, J=12.6 Hz, 1.8 Hz, 1H), 7.62☐ (d, J=6.9 Hz, 1H), 740 (d, J=8.7 Hz, 1H), 7.26 (d, J=8.7 Hz, 1H), 6.19 (d, J=7.2 Hz, 1H).

The Preparation of Diethyl 8-nitroquinolin-3-yl phosphonate (10c)

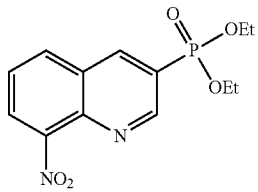

10c

Compound 3c (30 g), KOAc (23.4 g), HPO(OEt)2 (18.4 mL), toluene (300 mL) and Pd(dppf)2Cl2.CH2Cl2 (1 g) were added to flask in sequence under N₂. The resulting mixture was refluxed for 3 hours, diluted with EtOAc, filtered through Silica gel, and concentrated to afford 10c 46 g.

1H NMR (300 MHz, CDCl3) δ 9.28 (dd, J=1.8 Hz, 4.2 Hz, 1H), 8.82 (dd, J=1.8 Hz, 15 Hz, 1H), 8.16 (t, J=6 Hz, 2H), 7.21 (d, J=7.5 Hz, 1H), 7.74 (t, J=8.1 Hz, 1H), 4.33-4.11 (m, 4H), 1.37 (t, J=6.9 Hz, 6H).

The Preparation of 8-nitroquinolin-3-yl phosphonic acid (11c)

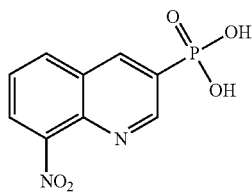

11c

Compound 10c (44.5 g) was added to 48% HBraq (230 mL). The resulting mixture was refluxed for 4 hours. The mixture was cooled, evaporated to dryness. The solid was washed with EtOH/EtOAc for 2 hours, and suction-filtered. A yellow solid 11c 31.5 g was given.

1H NMR (300 MHz, D20) δ 9.18 (dd, J=□1.8 Hz, 6 Hz, 1H), 8.98 (dd, J=1.8 Hz, 13.2 Hz, 1H), 8.54 (d, J=7.8 Hz, 1H), 8.36 (d, J=8.4 Hz, 1H), 7.81 (t, J=7.8 Hz, 1H).

The preparation of 8-nitroquinolin-3-yl phosphonic dichloride (12c)

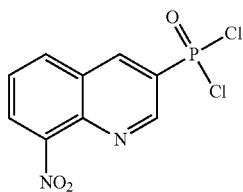

12c

Compound 11c (50.3 g) was added to dichloroethane (650 mL), and then DMF (3.6 mL) was added. Then (COCl)₂ (42 mL) was added dropwise under ice bath. After the addition was complete, the resulting mixture was refluxed for overnight. The mixture was cooled, and evaporated to dryness to yield 12c which was immediately used in the subsequent reaction.

The Preparation of (4S)-4-(3-chlorophenyl)-2-(8-nitroquinolin-3-yl)-1,3,2-dioxaphosphinan-2-one (13c)

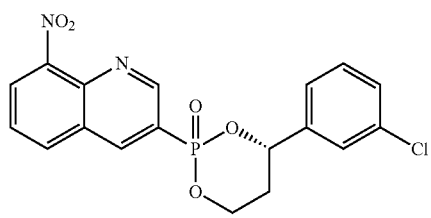

13c (S)-1-(3-chlorophenyl)propane-1,3-diol (36.95 g) 20 was added to CH₂Cl₂ (540 mL). Then TiCl₄ was added (22 mL) dropwise under −78° C. The mixture was stirred for 5 minutes, and then stirred for 5 minutes under ice bath. TEA (110 mL) was added to the mixture. The resulting mixture was added dropwise to the solution of compound 12c in dichloromethane. After the addition was complete, the resulting mixture reacted at room temperature for overnight. The reaction mixture was diluted with CH₂Cl₂ (700 mL), charged with 10% tartaric acid (210 mL), and stirred for 2 minutes. The mixture was filtered through celite, extracted with CH₂Cl₂. The organic layer was dried over Na₂SO₄, and the solvent removed. The residue was recrystallized twice from CH₃CN. A yellow solid 13c 35.5 g was given in 44%. m/z: 405.1 [M+1];

The Preparation of (4S)-4-(3-chlorophenyl)-2-(8-aminoquinolin-3-yl)-1,3,2-dioxaphosphinan-2-one (14c)

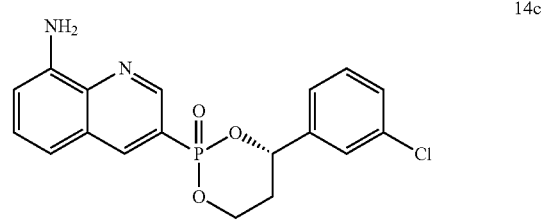

14c

Compound 13c (62.9 g) was added to EtOH (160 mL) and AcOH (160 mL). Then Fe (43.6 g) was added. The resulting mixture reacted at 40° C. for 10 minutes, cooled, adjusted to pH 6 with sat. NaHCO₃ solution, extracted with CH₂Cl₂. The organic layer was dried over Na₂SO₄, and evaporated. A yellow solid 14c 50 g was given in 86%. m/z: 375.0 [M+1];

The Preparation of (4S)-4-(3-chlorophenyl)-2-(8-((2,2-dimethyl-1,3-dioxane-4,6-dione)-5-methylene) aminoquinolin-3-yl)-1,3,2-dioxaphosphinan-2-one (15c)

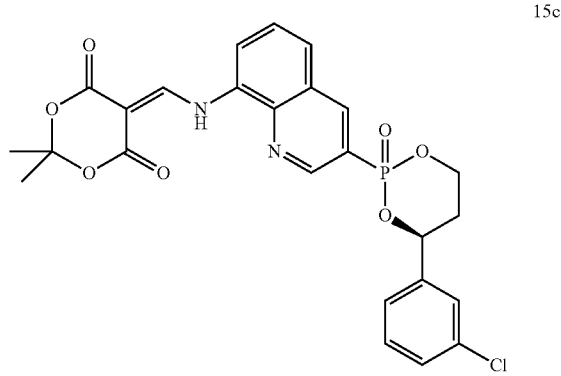

15c

Compound 14c (49 g) was added to EtOH (320 mL). then 5-(ethoxymethylene)-2,2-dimethyl-1,3-dioxane-4,6-dione 17 (31.4 g) was added. The resulting mixture was refluxed for 2 hours, cooled, and suction-filtered. A yellow solid 15c 60 g was given in 87%. m/z: 529.0 [M+1], 471.0 was found.

The Preparation of (4S)-4-(3-chlorophenyl)-2-(7-hydroxy-1,10-phenanthrolin-3-yl)-1,3,2-dioxaphosphinan-2-one (16c)

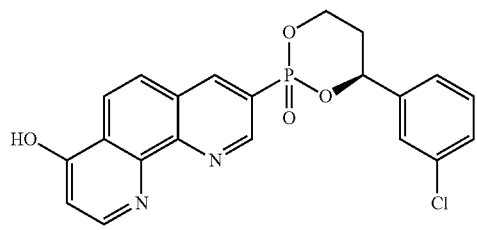

16c

Diphenyl ether was heated to boiling, compound 15c (3 g) was added to rapidly. The resulting mixture was refluxed for 50 s. The mixture was cooled to 100° C., poured into petroleum ether, and suction-filtered. The cake was purified with chromatography (DCM:MeOH=30:1). A yellow solid 16c 1.676 g was given in 70%.

1H NMR (300 MHz, DMSO) δ 12.53 (s, 1H), 9.34 (dd, J=2.1 Hz, 5.1 Hz, 1H), 9.15 (dd, J=1.8 Hz, 15.3 Hz, 1H), 8.27 (d, J=8.7 Hz, 1H), 8.12-7.98 (m, 2H), 7.56 (s, 1H), 7.47-7.43 (m, 3H), 6.36 (d, J=7.2 Hz, 1H), 5.96 (d, J=11.1 Hz, 1H), 4.88-4.76 (m, 1H), 4.65-4.55 (m, 1H), 2.68-2.54 (m, 1H), 2.34-2.22 (m, 1H).

The Preparation of methyl 3-(3-chlorophenyl)-3-oxopropanoate (18)

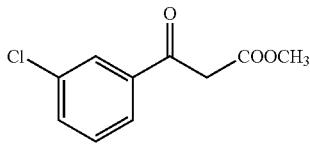

18

Potassium t-butoxide (15 g) was added to THF (50 mL) under nitrogen. The mixture was stirred at room temperature for 15 minutes. 1-(3-chlorophenyl) ethanone (10 g) and dimethyl carbonate (11 mL) was added slowly to the flask under ice bath. The mixture was stirred at room temperature for 1.5 hour. The reaction mixture was charged with water (40 mL) and concentrated hydrochloric acid (1.3 ml) and stirred for 15 minutes.

The organic layers were separated and the aqueous phase was extracted again with toluene. The combined organic extracts were washed with saturated brine, dried with NaSO$_4$, filtered and evaporated to dryness. A brown oil 18 13.22 g was given in 96%.

The Preparation of (3S)-methyl 3-(3-chlorophenyl)-3-hydroxypropanoate (19)

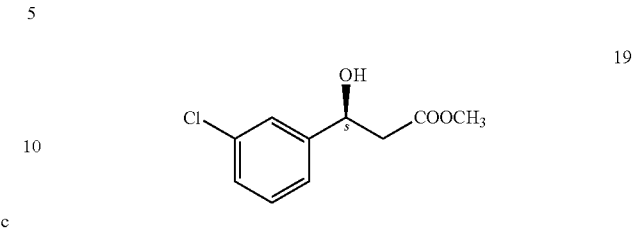

19

The triethylamine (5.38 g) was added dropwise slowly to formic acid (9.8 g) under nitrogen under ice bath. After the addition was complete, the mixture was stirred for 20 minutes and then reacted at room temperature for 1 hour. Compound 18 (11.3 g), DMF (45 mL) and (S,S)-Ts-DPEN-Ru—Cl-(p-cymene) (68 mg) were added to the flask. The resulting mixture reacted at 60° C. for overnight, was cooled to room temperature, charged with water (100 mL), extracted with EA. The organic layer was washed with brine, dried over anhydrous Na$_2$SO$_4$, filtered, evaporated to dryness, and purified with chromatography (EA:PE=1:10). A jacinth oil 10.434 g was given in 91%.

1H NMR (300 MHz, CDCl3) δ 7.45 (s, 1H), 7.37-7.27 (m, 3H), 5.16 (t, J=6.9 Hz, 1H), 3.78 (s, 3H), 2.78 (d, J=1.8 Hz, 1H), 2.76 (s, 1H).

The Preparation of (1S)-1-(3-chlorophenyl)propane-1,3-diol (20)

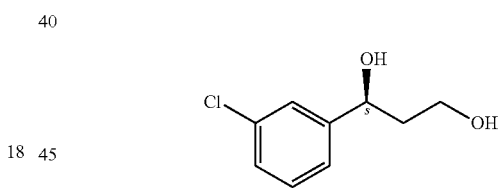

20

Sodium borohydride (1.84 g) and water (0.62 mL) were added to 1-butanol (37.5 mL), and then the solution of compound 19 (10.4 g) in 1-butanol (3.8 mL) was added dropwise to under ice bath. After addition was complete, the mixture was stirred for 0.5 h, and reacted at 90° C. for 4 h. The reaction mixture was cooled to room temperature, charged with aqueous potassium carbonate solution (10%, 23 mL), and stirred for 10 min. The organic layers were separated, washed with aqueous potassium carbonate solution (10 wt/vol %, 8 mL) and brine (8 mL), dried over anhydrous Na$_2$SO$_4$, filtered, evaporated to dryness, and purified with chromatography (DCM:CH$_3$OH=30:1). A yellow oil 20 7.75 g was given in 85.5%.

1H NMR (300 MHz, CDCl3) δ 7.36 (s, 1H), 7.30-7.20 (m, 3H), 4.92 (q, J=4.5□ Hz, 7.8 Hz, 1H), 3.90-3.79 (m, 2H), 2.82 (s, 2H), 2.03-1.85 (m, 2H).

The Preparation of 3-(4S-4-(3-chlorophenyl)-1,3,2-dioxaphosphinan-2-one-2-yl)-1,10-phenanthrolin-7-yl phosphoric acid (22)

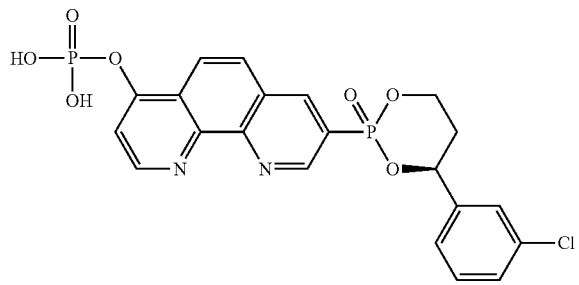

22

Compound 16c (2 g) was dissolved in dichloromethane (100 mL). Triethylamine (2 mL) and 4-dimethylamino pyridine (57 mg) were added to the reaction mixture. The reaction mixture was putted under ice bath. Diethyl chlorophosphate (2 mL) in dichloromethane (20 mL) was added dropwise slowly to the reaction mixture. The mixture was allowed to react for one hour under ice bath and then 2 hours at room temperature. The reaction mixture was poured into saturated brine (200 mL). The organic layer was separated and the aqueous layer was extracted with dichloromethane. The organic layers were combined, dried over anhydrous sodium sulfate, rotary evaporated to dryness, and purified with chromatography (DCM:CH₃OH=100:1) to yield 21 1.7 g. 21 (1.7 g) was dissolved in DCM (2 mL). Trimethylsilyl bromide (4 mL) was added to the mixture in one time under ice bath. After reacted 1 hr under ice bath, diethyl ether (50 mL) was added to the reaction mixture. The resulting mixture was filtered. The cake was collected, dissolved in methanol (20 mL), and stirred for 10 minutes. The reaction mixture was rotary evaporated to dryness and purified with chromatography (DCM:CH₃OH:CH₃COOH=20:1:0.05 DCM:H₃OH=4:1). A white solid 22 600 mg was given in 25% yield.

m/z: 507.0 [M+1];

☐1H NMR (300 MHz, dmso) δ 13.84 (m, 1H), ☐9.27 (dd, J=4.8, 1.8 Hz, 1H), 8.99 (dd, J=14.3, 1.8 Hz, 1H), 8.39 (d, J=7.1 Hz, 1H), 8.30 (d, J=8.9 Hz, 1H), 8.13 (d, J=9.0 Hz, 1H), 7.50 (s, 1H), 7.45-7.38 (m, 1H), 7.35-7.25 (m, 2H), 6.85 (d, J=7.1 Hz, 1H), 5.35 (dd, J=9.0, 5.9 Hz, 1H), 4.11-3.98 (m, 2H), 2.68-2.55 (m, 1H), 2.50-2.34 (m, 1H).

The Preparation of Disodium 3-(4S-4-(3-chlorophenyl)-1,3,2-dioxaphosphinan-2-one-2-yl)-1,10-phenanthrolin-7-yl phosphate (23)

23

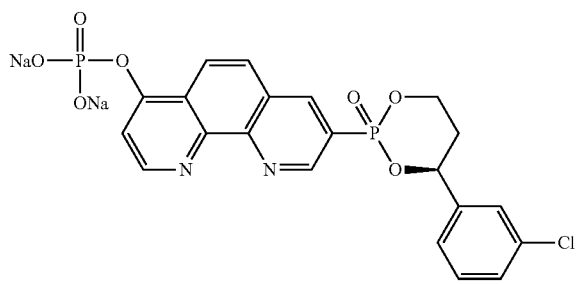

Compound 22 (500 mg) was suspended to methanol (10 mL), 1N NaHCO₃ solution (2 mL) was added to the mixture slowly at room temperature. The reaction mixture was allowed to stir for 20 minutes, and evaporated to dryness. A white solid 23 540 mg was given in 100% yield.

m/z: 550.0 [M+1], found 507;

1H NMR (300 MHz, dmso) δ 9.27 (dd, J=4.8, 1.8 Hz, 1H), 8.99 (dd, J=14.3, 1.8 Hz, 1H), 8.39 (d, J=7.1 Hz, 1H), 8.30 (d, J=8.9 Hz, 1H), 8.13 (d, J=9.0 Hz, 1H), 7.50 (s, 1H), 7.45-7.38 (m, 1H), 7.35-7.25 (m, 2H), 6.85 (d, J=7.1 Hz, 1H), 5.35 (dd, J=9.0, 5.9 Hz, 1H), 4.11-3.98 (m, 2H), 2.68-2.55 (m, 1H), 2.50-2.34 (m, 1H).

The Preparation of di-t-butyl (3-(4S-4-(3-chlorophenyl)-1,3,2-dioxaphosphinan-2-one-2-yl)-1,10-phenanthrolin-7-oxy)-7-methyl phosphate (24) and di-t-butyl (3-(4S-4-(3-chlorophenyl)-1,3,2-dioxaphosphinan-2-one-2-yl)-1,10-phenanthrolin-7-one)-10(7H)-methyl phosphate (25)

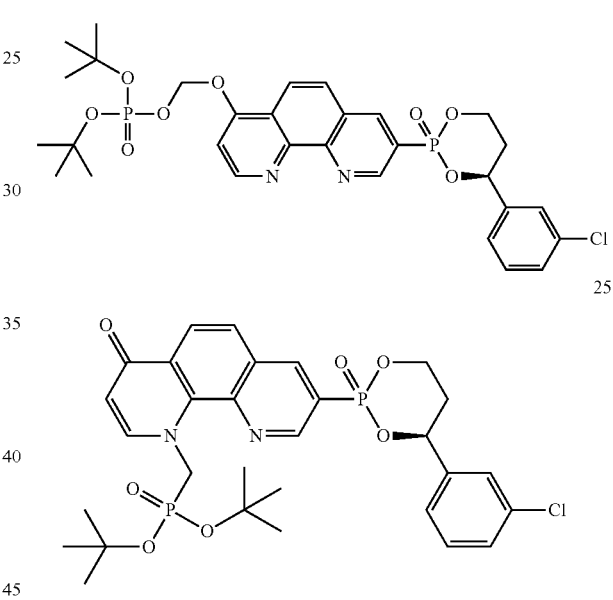

Compound 16c (200 mg, 0.47 mmol) was dissolved in DMSO (2 mL). Potassium carbonate (195 mg, 1.41 mmol) was added to the reaction mixture. The resulting mixture was stirred for 15 minutes under 30° C. Di-t-butyl chloromethyl phosphate (146 mg, 0.56 mmol) was added to the reaction mixture and the resulting mixture reacted at 30° C. for overnight. The reaction mixture was poured into saturated brine (20 mL). The organic layer was separated and the aqueous layer extracted with dichloromethane. The organic layers were combined, dried over sodium sulfate, rotary evaporated to dryness and purified with chromatography (EA) to yield intermediate 24 and 25.

m/z: 649.2[M+1];

Compound 24:

1H NMR (300 MHz, dmso) δ 9.48 (dd, J=4.9, 1.9 Hz, 1H), 9.14 (dd, J=15.4, 1.9 Hz, 1H), 9.10 (d, J=5.3 Hz, 1H), 8.31 (d, J=9.1 Hz, 1H), 7.63-7.58 (m, 2H), 7.55-7.41 (m, 3H), 6.11-5.91 (m, 3H), 4.92-4.75 (m, 1H), 4.71-4.53 (m, 1H), 2.73-2.55 (m, 1H), 2.36-2.19 (m, 1H), 1.37 (s, 18H)

13C NMR (75 MHz, dmso) δ 158.59, 151.37, 150.71, 150.54, 147.15, 146.18, 142.12, 142.01, 141.71, 133.29, 130.57, 128.41, 126.26, 125.79, 124.59, 121.53, 120.83, 106.97, 87.59, 82.98, 77.56, 66.24, 33.30, 29.38

Compound 25:

1H NMR (300 MHz, dmso) δ 9.39 (dd, J=4.6, 2.1 Hz, 1H), 9.19 (dd, J=15.6, 2.0 Hz, 1H), 8.43 (d, J=8.7 Hz, 1H), 8.22 (d, J=8.1 Hz, 1H), 8.18 (d, J=8.4 Hz, 1H), 7.58 (s, 1H), 7.50-7.44 (m, 3H), 7.18-6.99 (m, 2H), 6.49 (d, J=7.9 Hz, 1H), 5.98 (d, J=11.2 Hz, 1H), 4.93-4.72 (m, 1H), 4.69-4.49 (m, 1H), 2.72-2.52 (m, 1H), 2.34-2.19 (m, 1H), 1.21 (s, 9H), 1.19 (s, 9H).

13C NMR (75 MHz, dmso) δ 176.22, ☐148.52, 147.50, 142.91, 141.99, 141.88, 136.23, 133.28, 130.54, 129.08, 128.91, 128.46, 125.72, 125.00, 124.60, 124.08, 121.52, 112.53, 82.30, 80.38, 77.54, 66.52, 33.21, 29.16.

(3-(4S-4-(3-chlorophenyl)-1,3,2-dioxaphosphinan-2-one-2-yl)-1,10-phenanthrolin-7-oxy)-7-methyl phosphoric acid (26)

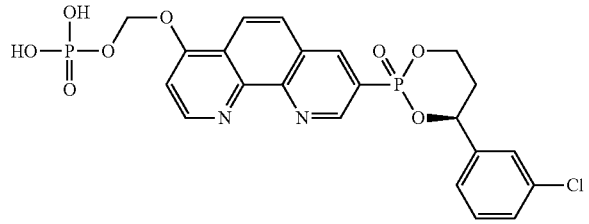

26

Compound 24 (50 mg, 0.08 mmol) was dissolved in dichloromethane (3 mL). TFA (1 mL) was added to the mixture at room temperature. The reaction mixture was stirred for 30 minutes at room temperature. The reaction mixture was evaporated to dryness. Methanol (1 mL) was added to the residue, and the mixture was suction-filtered to afford compound 26.

1H NMR (300 MHz, dmso) δ 9.46 (dd, J=05.0, 1.8 Hz, 1H), 9.23-9.05 (m, 2H), 8.37-8.21 (m, 2H), 7.68 (d, J=5.6 Hz, 1H), 7.56 (s, 1H), 7.51-7.36 (m, 3H), 6.12-5.90 (m, 3H), 4.90-4.74 (m, 1H), 4.71-4.50 (m, 1H), 2.71-2.54 (m, 1H), 2.33-2.21 (m, 1H)

The Preparation of (3-(4S-4-(3-chlorophenyl)-1,3,2-dioxaphosphinan-2-yl)-1,10-phenanthrolin-7-one)-10(7H)-methyl phosphoric acid (27)

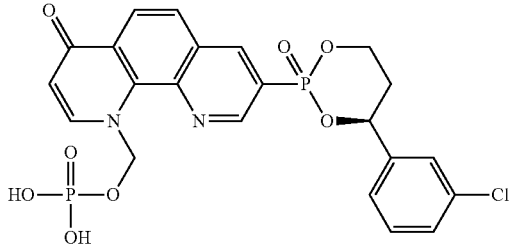

27

Compound 25 (50 mg, 0.08 mmol) was dissolved in dichloromethane (3 mL). TFA (1 mL) was added to the mixture at room temperature. The reaction mixture was stirred for 30 minutes at room temperature. The reaction mixture was evaporated to dryness. Methanol (1 mL) was added to the residue, and the mixture was suction-filtered to afford compound 27.

1H NMR (300 MHz, dmso) δ 9.38 (dd, J=4.5, 2.0 Hz, 1H), 9.13 (dd, J=15.6, 2.0 Hz, 1H), 8.40 (d, J=8.7 Hz, 1H), 8.19 (d, J=8.3 Hz, 1H), 8.13 (d, J=8.7 Hz, 1H), 7.58 (s, 1H), 7.54-7.35 (m, 3H), 7.04 (t, J=9.9 Hz, 1H), 6.91 (t, J=9.8 Hz, 1H), 6.43 (d, J=7.8 Hz, 1H), 5.95 (d, J=10.8 Hz, 1H), 4.88-4.76 (m, 1H), 4.69-4.45 (m, 1H), 2.74-2.56 (m, 1H), 2.31-2.22 (m, 1H).

Example 2. Expression and Purification of P4H

Human recombinant P4H was expressed in *E. coli*. Briefly, DNA encoding the signal sequence of P4H was cloned into pET28_N-His_TEV, the resulting plasmid pET28_N-His_TEV_P4HA1/PDI was transferred to *E. coli* Origami2(DE3) to co-expressed. The enzyme obtained was purified with MonoQ ion-exchange column, TEV digested and confirmed by MS, passed through Histrap HP column, finally purified with Hiload16/60 superdex 200 column.

Example 3. Assays of the Enzymatic Activity of P4H and the Influence of the Compound of the Present Invention to the Enzymatic Activity The measurement of the enzymatic activity of purified P4H zymoprotein and the assay of the influence of the compound to the enzymatic activity were performed at the following coupling enzymatic reaction system: 100 mM Tris (pH7.0), 0.1 mM $(NH_4)_2Fe(SO_4)_2$, 0.1 mM ascorbic acid, 0.2 mM CoA, 0.2 mM ATP, 0.5 uM succinyl CoA synthase, 100 uM 2-oxoglutarate, 100 uM (Pro-Pro-Gly)$_{10}$peptide, 50 nM P4H enzyme, 50 ul total. After 45 min reaction at 25° C., 10 ul MLG R1 was added and reacted for 10 min, 10 ul MLG R2 was added and reacted for 20 min. P4H catalyst 2-oxoglutaric acid and polypeptide with coenzyme and suitable enzyme reaction environment to give product succinic acid. The product succinic acid then produced succinyl CoA and phosphoric acid with the action of succinyl CoA synthase. The level of generated phosphoric acid could be measured by MLG, which reflects the level of P4H. The generated green product $(MG+)(H_2PMo_{12}O_{40})$ was measured at OD 630 nm.

The evaluation of the inhibition of compound about P4H enzyme was performed in 96-well plates. Every concentration has two duplicate samples (n=2). Compound 9c was added to the enzymatic reaction system in following concentrations (in sequence and before the addition of P4H enzyme): 0.01, 0.03, 0.1, 0.3, 1, 3, 30, 100, 300 nM. Data analysis and statistics was performed by Prism. IC50 of compound 9c to enzyme is 8.1 μM (FIG. 1). FIG. 1 indicates, the inhibition of compound 9c to the activity of human P4H enzyme is higher as the concentration of 9c is higher.

Example 4. Studies of In-Vivo Pharmacokinetic

Wistar rats (200±20 g) were divided into 2 groups, 6 each, half female and half male in each group, ate and drank freely. The first group was given compound 16c 3 mg·kg$^{-1}$ caudal-intravenously. The second group was orally administered disodium salt of compound 27 (39 mg·kg$^{-1}$). Blood (0.3 mL) was collected from retroorbital vein at time point 0 h, 0.08 h, 0.17 h, 0.33 h, 0.5 h, 0.75 h, 1 h, 1.5 h, 2 h, 3 h, 5 h, 7 h, placed into cold heparinized Eppendorf tubes.

The samples were centrifuged at 4° C. (15000 rpm) for 5 min. Transfer 100 μL plasma sample to −80° C. freezer for test.

Figure 2:
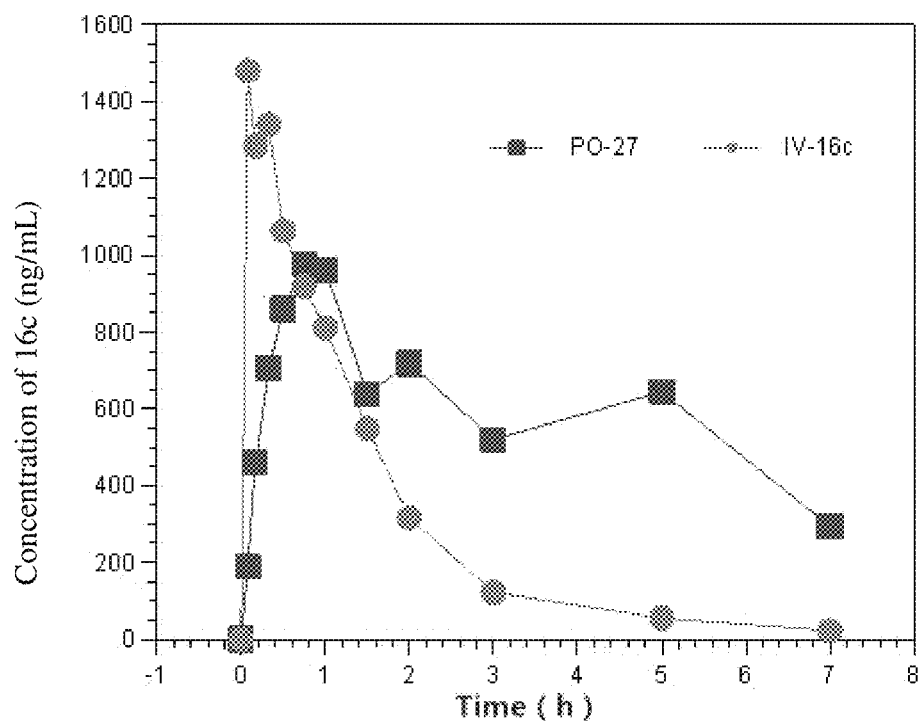
FIG. 2. Concentration-time curve of compound 16c in plasma after iv dosing 16c (3 mg/kg) and PO dosing 27 (39 mg/kg).

Quantitative LC-MS/MS analysis methods of compound 9c and prodrug 16c in plasma were set up, using diazepam and mildronate as internal standard, respectively. (Prodrug 27 was not detected under experimental condition from plasma) the plasma sample was tested and analyzed. (result see in Table 1 and FIG. 2)

TABLE 1

The concentration of compound 16c in plasma after compound 16c iv dosing and compound 27 PO dosing

| Compound | Route of administration | $C_{max}$* (ng · mL$^{-1}$) | $t_{1/2}$** (h) | $AUC_{0-t}$*** (μg · h · L$^{-1}$) | $AUC_{0-\infty}$**** (μg · h · L$^{-1}$) |
|---|---|---|---|---|---|
| 16c | IV | 1617.80 | 1.50 | 2064.58 | 2136.40 |
| 27 | PO | 1440 | 2.79 | 5235.70 | 6805.74 |

*$C_{max}$ refers to peak concentration in plasma
**$t_{1/2}$ refers to half life of drug in plasma
***$AUC_{0-t}$ refers to area under concentration-time curve until final test time
****$AUC_{0-\infty}$ refers to area under concentration-time curve until total clearance of drug Oral Bioavailability:

Oral Bioavailability was calculated according to compound 16c in plasma. Area under concentration-time curve (AUC) of PO dosing was divided by AUC of iv dosing of same amount of drugs, expressed as absorption percentage: Bioavailability (F)=AUCpo·Miv/AUCiv·Mpo×100%. Wherein, Miv means the molar concentration of drugs by iv dosing, and Mpo means the molar concentration of drugs by PO dosing. The $AUC_{0-t}$ of compound 16c in plasma After compound 16c (3 mg·kg$^{-1}$) was intravenously administered and compound 27 (39 mg·kg$^{-1}$) was orally administered, the $AUC_{0-t}$ of compound 16c in plasma is 2064.58 g·h/mL and 5235.70 g·h/mL, respectively. Based on the concentration of compound 16c in plasma, the bioavailability (F) of compound 27 is 25.4% (i.e 5235.70/(2064.58×10)×100%).

Concentration of Compound 16c and 9c in Liver:

16 Wistar rats (200±20 g) were divided into 4 groups randomly, female and male each half in each group, ate and drank freely before the experiment. After PO dosing of compound 27 (39 mg·kg$^{-1}$), rats were sacrificed at each time point 15 min, 45 min, 8 h, 24 h. Liver samples were collected, washed off blood and contents with saline, cut into small pieces, and stirred evenly. 1 g was weighed. 1 mL Methanol/water was added. After homogenated, additional 1 mL methanol/water was added. The mixture was sonicated for 15 seconds, centrifuged (4500 rpm) for 10 minutes. The upper clear solution was tested using LC-MS/MS method to give the concentration of compound 16c and 9c in liver at different time points after administration (table 2). The results indicate that prodrug 27 converted to compound 16c in rat after PO dosing, and compound 16c converted to compound 9c in liver.

TABLE 2 concentration of compound 16c and 9c (ng · g$^{-1}$) in liver at different time points after oral administration of compound 27

|  | 0.25 h | 0.75 h | 8 h | 24 h |
|---|---|---|---|---|
| 16c | 521.50 | 662.5 | 584.50 | 50.88 |
| 9c | 16.13 | 64.25 | 44.68 | 3.55 |

Example 5. Study of In-Vivo Pharmaceutical Efficacy

This experiment used Bile Duct Ligation to induce liver fibrosis model in rats. Treatment of BDL rats with PO dosing prodrug 27 was studied.

Briefly, Wistar rats (200±20 g) were divided into 3 groups, half female and half male in each group:

SHAM group: 6 rats were anaesthetized, the abdominal skin was shaved and sterilized regularly, the common bile duct was exposed by an upper abdominal midline incision with sterile operation. Muscle and skins were sutured separately.

liver fibrosis MODEL group: 12 rats were anaesthetized, the abdominal skin was shaved and sterilized regularly, the common bile duct was exposed and ligated by an upper abdominal midline incision with sterile operation. Muscle and skins were sutured separately.

Dosing group: 12 rats were anaesthetized, the abdominal skin was shaved and sterilized regularly, the common bile duct was exposed and ligated by an upper abdominal midline incision with sterile operation. Muscle and skins were sutured separately. After operation, disodium salt of compound 27 (30 mg/kg) was dissolved in water and dosed orally to the rats once per day test indexes:

After 2 weeks, measure the ALT and AST of serum and liver homogenate

After 2 weeks, rats were sacrificed, and liver performed HE staining and Masson staining.

The Influence of Compound 27 Orally Administrated on the ALT and AST of the Serium Homogenate of BDL Rats Having Liver Fibrosis ALT and AST were liver function index in common clinical use now. ALT mainly exists in the cytosol of hepatocyte, AST mainly exists in the mitochondria of hepatocyte. When hepatocyte is damaged, the level of ALT and AST in serum rise, which could reflect the level of the damage of hepatocyte. The ALT and AST of the serum and liver homogenate of rats in model group with BDL rised significantly. After compound 27 was administrated for 14 days, animals were sacrificed. The ALT and AST of the serium and liver homogenate of those animal decreased significantly, which have significant difference comparing with model group (**P<0.01, see on Table 3 and Table 4). It's indicated that compound 27 alleviated the level of the damage of liver function with BDL, and have protection effect to liver damage resulted from bile regurgitation.

TABLE 3

The influence of compound 27 on the ALT (IU/L) of the serium of BDL rats having liver fibrosis

| groups | ALT in serum | ALT in liver |
|---|---|---|
| SHAM | 67.1 ± 5.45 | 68.2 ± 8.33 |
| MODEL | 144.4 ± 15.94 | 136.8 ± 16.48 |
| Compound 27 (30 mg/kg) | 74.4 ± 17.82** | 76.4 ± 11.35** |

**P < 0.01, compared to MODEL group

TABLE 4

The influence of compound 27 on the AST (IU/L) of the serium of BDL rats having liver fibrosis

| groups | AST in serum | AST in liver |
|---|---|---|
| SHAM | 67.7 ± 4.67 | 67.40 ± 5.28 |
| MODEL | 207.2 ± 30.96 | 198.75 ± 27.70 |

TABLE 4-continued

The influence of compound 27 on the AST (IU/L) of the serium of BDL rats having liver fibrosis

| groups | AST in serum | AST in liver |
| --- | --- | --- |
| Compound 27 (30 mg/kg) | 87.2 ± 12.51** | 91.42 ± 8.79** |

**P < 0.01, compared to MODEL group

Figure 3:
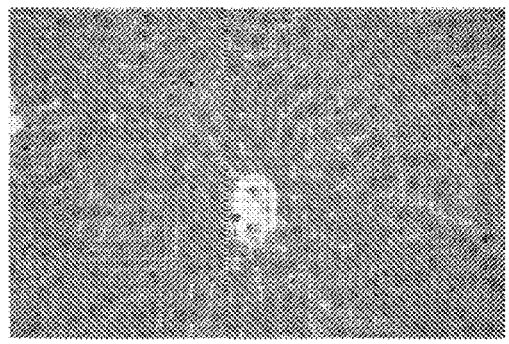
FIG. 3. H&E staining of rat liver (SHAM group)

The Influence of Compound 27 Orally Administrated on the HE Staining of BDL Rats Having Liver Fibrosis H&E staining results as follow:

Sham group: depicted in FIG. 3, the structure of hepatic lobule is normal, hepatocytes centre on central veins and radiate out in all directions. The hepatocytes in hepatic lobule range in order. The size of hepatocytes is even. There is no the degeneration and necrosis of hepatocytes.

Figure 4:
FIG. 4. H&E staining of rat liver (BDL 2 weeks)

Model group: depicted in FIG. 4, the structure of hepatic lobule is inordinate.

Hepatocytes swelling. The cytoplasm of hepatocytes is loose. The connective tissue of fibrosis proliferate.

Figure 5:
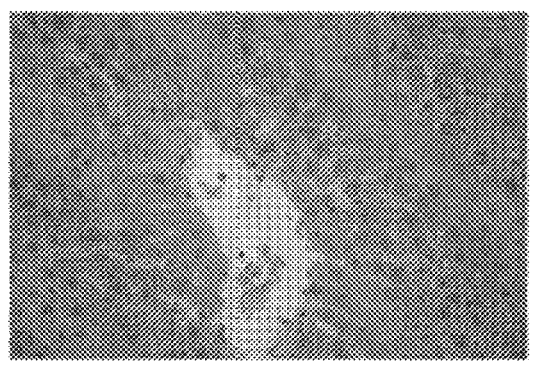
FIG. 5. H&E staining of rat liver (BDL, PO administration of 27, 30 mpk, 2 weeks)

Dosing group: depicted in FIG. 5, the treating group varies the pathological changes of hepatic tissue.

What is claimed is:

1. A compound of formula (I) or formula (II), or a pharmaceutically acceptable salt thereof:

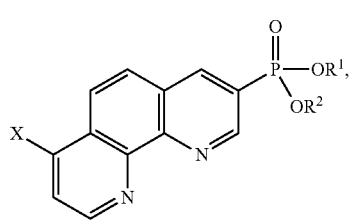
(I)

wherein:
X is —Cl or —OR$^3$, wherein R$^3$ is selected from —H, —C(O)—(C$_1$-C$_6$ alkyl), —PO(OH)$_2$ and —CH$_2$OPO(OH)$_2$, R$^1$ and R$^2$ can be independently selected from H, C$_1$-C$_6$ alkyl, —CH$_2$OCO—(C$_1$-C$_6$ alkyl) and —CH$_2$OCOO—(C$_1$-C$_6$ alkyl), or R$^1$ and R$^2$ join to form a group having the formula:

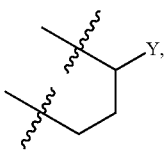

wherein Y is aryl or heteroaryl;

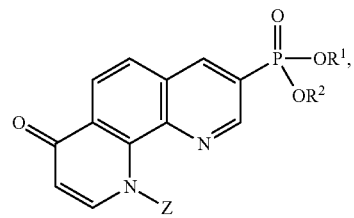
(II)

wherein:
Z is selected from —H and —CH$_2$OPO(OH)$_2$,
R$^1$ and R$^2$ can be independently selected from H, C$_1$-C$_6$ alkyl, —CH$_2$OCO—(C$_1$-C$_6$ alkyl) and —CH$_2$OCOO—(C$_1$-C$_6$ alkyl), or R$^1$ and R$^2$ join to form a group having the formula:

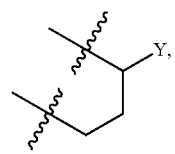

wherein Y is aryl or heteroaryl.

2. The compound or pharmaceutically acceptable salt thereof of claim 1, wherein X in formula (I) is —OH, —OPO(OH)$_2$ or —OCH$_2$OPO(OH)$_2$.

3. The compound or pharmaceutically acceptable salt thereof of claim 1, wherein R$^1$ and R$^2$ in formula (I) are H; alternatively, R$^1$ and R$^2$ in formula (I) together form a group having the formula:

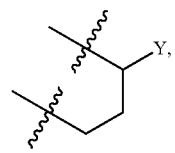

wherein Y is aryl;
alternatively, R$^1$ and R$^2$ in formula (I) together form a group having the formula:

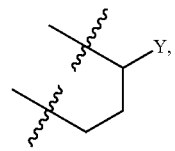

wherein Y is heteroaryl.

4. The compound or pharmaceutically acceptable salt thereof of claim 1, wherein the compound is selected from:

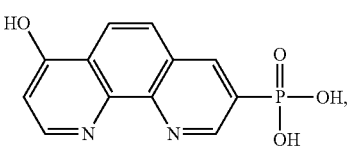

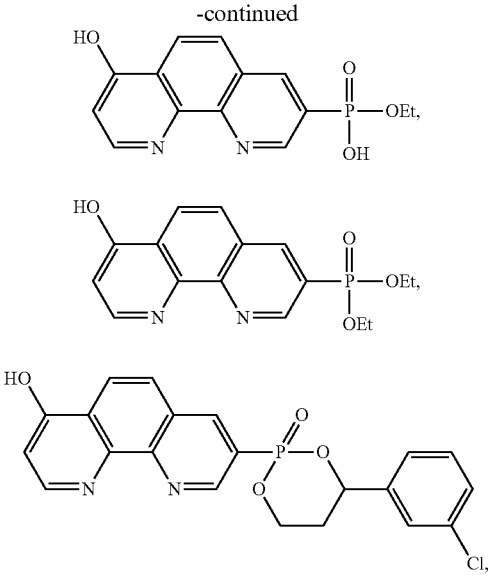

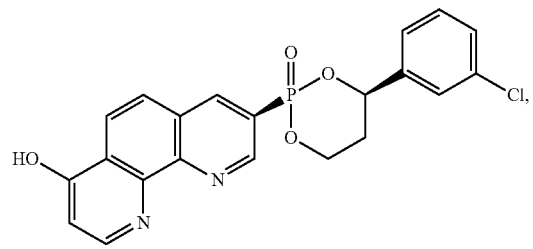

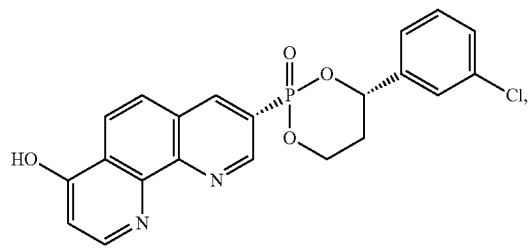 [SMILES: O=P1(c2cnc3c(ccc4c(O)ccnc43)c2)OCCC(c2cccc(Cl)c2)O1]

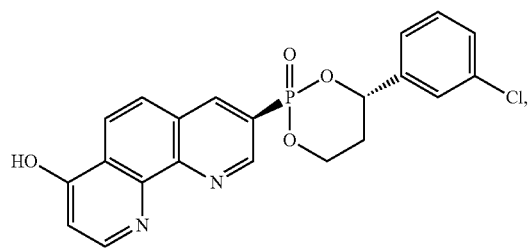

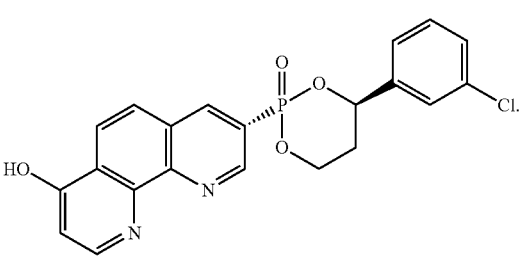

5. The compound or pharmaceutically acceptable salt thereof of claim 4, wherein the compound having the structure:

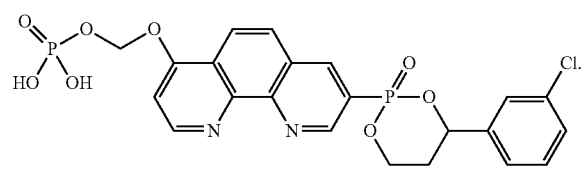

6. The compound or pharmaceutically acceptable salt thereof of claim 5, wherein the compound is selected from:

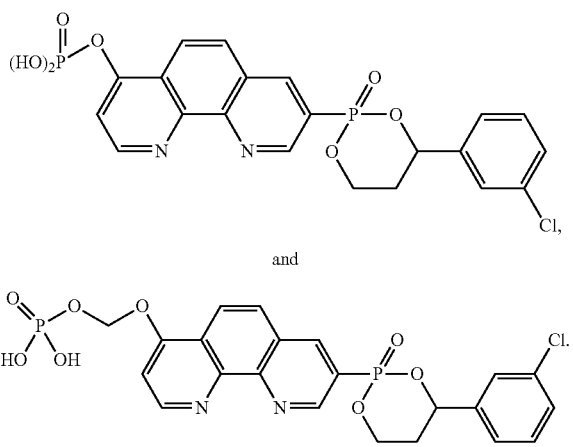

7. The compound or pharmaceutically acceptable salt thereof of claim 4, wherein the compound is selected from:

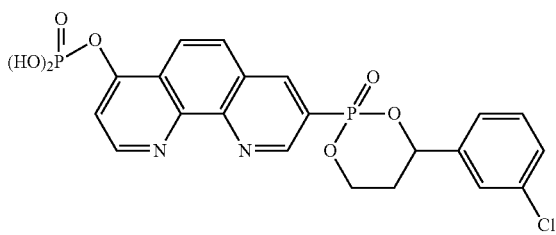

and

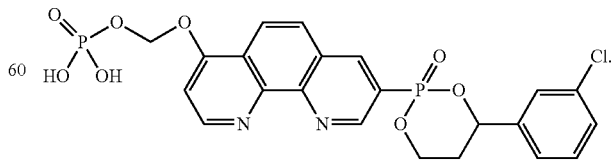

8. The compound or pharmaceutically acceptable salt thereof of claim 7, wherein the compound is selected from:

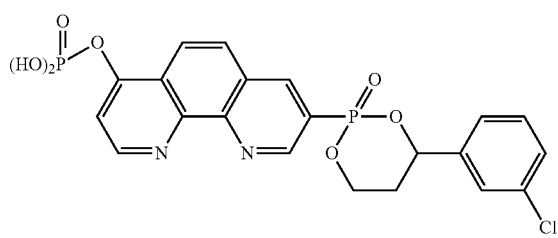

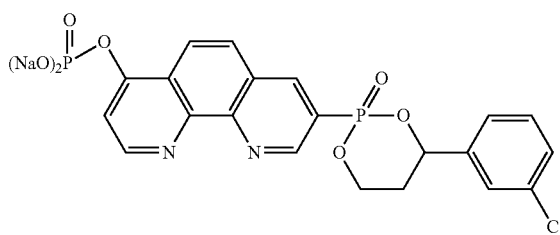

and

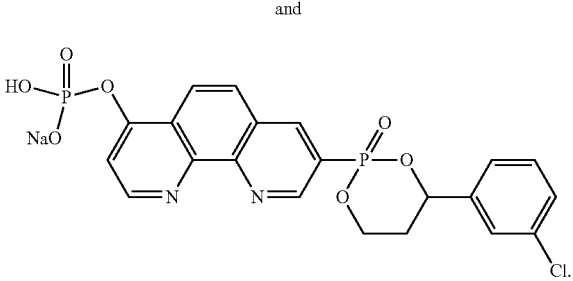

9. The compound or pharmaceutically acceptable salt thereof of claim 7, wherein the compound is selected from:

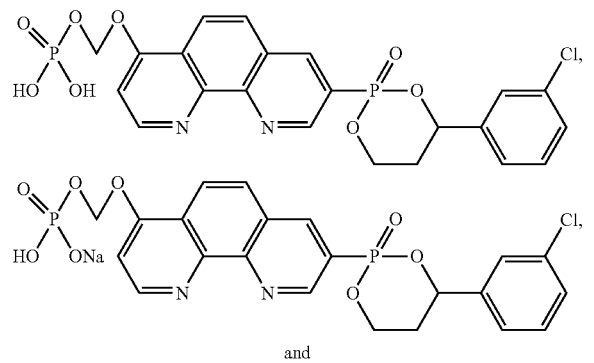

and

10. The compound of claim 1, wherein the Z in formula (II) is —CH$_2$OPO(OH)$_2$.

11. The compound of claim 1, wherein R$^1$ and R$^2$ in formula (II) are H, alternatively, R$^1$ and R$^2$ in formula (II) together form a group having the formula:

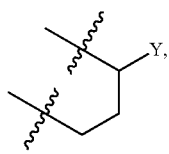

Wherein Y is aryl, alternatively, R$^1$ and R$^2$ in formula (II) together form a group having the formula:

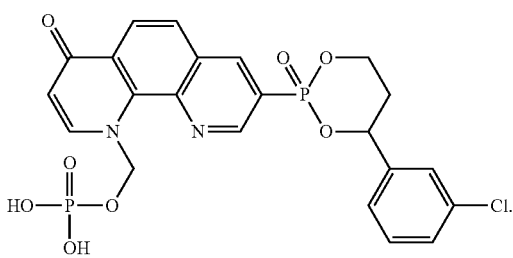

wherein Y is heteroaryl.

12. The compound or pharmaceutically acceptable salt thereof of claim 1, wherein the compound of formula II having the structure:

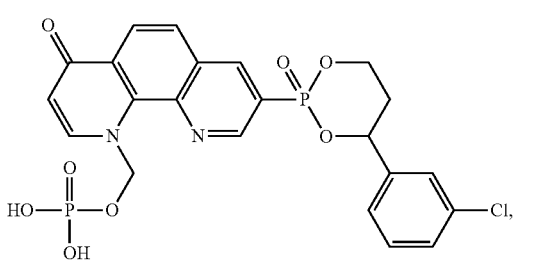

13. The compound or pharmaceutically acceptable salt thereof of claim 12, wherein the compound is selected from:

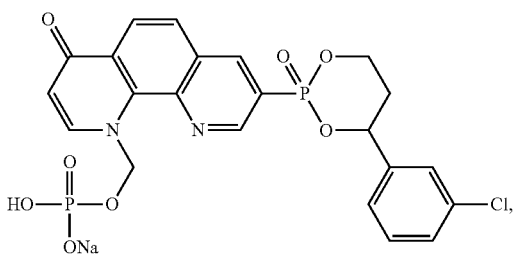

and

-continued

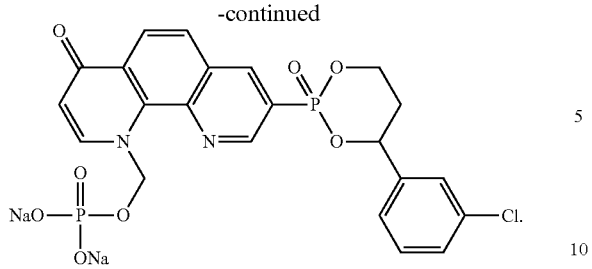

14. A pharmaceutical composition comprising a compound of claim 1 or a pharmaceutically acceptable salt thereof and a pharmaceutical carrier.

15. A method for inhibiting collagen prolyl-4-hydroxylase in a subject in need thereof, comprising: administering an effective amount of the compound according to claim 1 or pharmaceutically acceptable salt thereof to the subject.

16. A method of treating liver fibrosis in a subject in need thereof, comprising: administering an effective amount of the compound or pharmaceutically acceptable salt thereof according to claim 1 to the subject.

* * * * *